(12) United States Patent
Low et al.

(10) Patent No.: US 8,388,977 B2
(45) Date of Patent: Mar. 5, 2013

(54) DIAGNOSIS OF MACROPHAGE MEDIATED DISEASE

(75) Inventors: Philip S Low, West Lafayette, IN (US); Mary Jo Turk, New York, NY (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/529,823

(22) Filed: Jun. 21, 2012

(65) Prior Publication Data

US 2012/0301397 A1 Nov. 29, 2012

Related U.S. Application Data

(60) Continuation of application No. 11/648,223, filed on Dec. 29, 2006, now abandoned, which is a division of application No. 10/138,275, filed on May 2, 2002, now Pat. No. 7,740,854.

(60) Provisional application No. 60/288,208, filed on May 2, 2001.

(51) Int. Cl.
*A61K 39/385* (2006.01)
*A61K 35/26* (2006.01)

(52) U.S. Cl. .................................. 424/191.1; 424/577

(58) Field of Classification Search ........................ None
See application file for complete search history.

(56) References Cited

U.S. PATENT DOCUMENTS

| | | | |
|---|---|---|---|
| 2,816,110 A | 12/1957 | Sletzinger et al. |
| 4,577,636 A | 3/1986 | Spears |
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |
| 6,960,449 B2 | 11/2005 | Wang et al. |
| 7,033,594 B2 | 4/2006 | Low et al. |
| 7,128,893 B2 | 10/2006 | Leamon et al. |
| 7,223,380 B2 | 5/2007 | Yang et al. |
| 7,381,535 B2 | 6/2008 | Perez et al. |
| 7,601,332 B2 | 10/2009 | Vlahov |
| 7,740,854 B2 | 6/2010 | Low et al. |
| 8,043,602 B2 | 10/2011 | Jallad et al. |
| 8,043,603 B2 | 10/2011 | Kennedy et al. |
| 2001/0031252 A1 | 10/2001 | Low et al. |
| 2002/0127181 A1 | 9/2002 | Edwards et al. |
| 2003/0198643 A1 | 10/2003 | Lu |
| 2003/0219375 A1 | 11/2003 | Worms |

(Continued)

FOREIGN PATENT DOCUMENTS

| | | |
|---|---|---|
| EP | 0220030 | 10/1986 |
| EP | 0273085 | 12/1986 |

(Continued)

OTHER PUBLICATIONS

Yang, D. J. et al., "Imaging-Tumor Folate Receptors Using Radiolabeled Folate and Methotrexate." *Journal of Labelled Compounds and Radiopharmaceuticals*, 1999, Sussex, GB, vol. Supp. 1, No. 42, June, pp. S696-S697.

(Continued)

*Primary Examiner* — Michail Belyavskyi
(74) *Attorney, Agent, or Firm* — Barnes & Thornburg LLP

(57) ABSTRACT

The invention relates to a method of treating or monitoring/diagnosing a disease state mediated by activated macrophages. The method comprises the step of administering to a patient suffering from a macrophage mediated disease state an effective amount of a composition comprising a conjugate or complex of the general formula $A_b\text{-}X$ where the group $A_b$ comprises a ligand capable of binding to activated macrophages, and when the conjugate is being used for treatment of the disease state, the group X comprises an immunogen, a cytotoxin, or a compound capable of altering macrophage function, and when the conjugate is being used for monitoring/diagnosing the disease state, X comprises an imaging agent. The method is useful for treating a patient suffering from a disease selected from the group consisting of rheumatoid arthritis, ulcerative colitis, Crohn's disease, inflammation, infections, osteomyelitis, atherosclerosis, organ transplant rejection, pulmonary fibrosis, sarcoidosis, and systemic sclerosis.

4 Claims, 15 Drawing Sheets

U.S. PATENT DOCUMENTS

| | | |
|---|---|---|
| 2004/0033195 A1 | 2/2004 | Leamon et al. |
| 2004/0057900 A1 | 3/2004 | Edwards et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0204565 A1 | 9/2006 | Low et al. |
| 2007/0009434 A1 | 1/2007 | Low et al. |
| 2007/0031334 A1 | 2/2007 | Leamon |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low |
| 2009/0012009 A1 | 1/2009 | Low et al. |
| 2010/0055735 A1 | 3/2010 | Low |
| 2010/0322854 A1 | 12/2010 | Low et al. |
| 2011/0044897 A1 | 2/2011 | Low et al. |
| 2012/0003151 A1 | 1/2012 | Low et al. |

FOREIGN PATENT DOCUMENTS

| | | |
|---|---|---|
| EP | 1940473 | 7/2008 |
| JP | 2774378 | 2/1998 |
| JP | 2003-515570 | 5/2003 |
| RU | 21 23338 | 11/1996 |
| WO | 90/12096 | 10/1990 |
| WO | 91/19501 | 12/1991 |
| WO | 91/19502 | 12/1991 |
| WO | WO 92/13572 | 2/1992 |
| WO | WO 96/22521 | 7/1996 |
| WO | 96/36367 | 11/1996 |
| WO | 97/37690 | 10/1997 |
| WO | WO 98/49196 | 11/1998 |
| WO | WO 00/73332 | 12/2000 |
| WO | 01/19320 | 3/2001 |
| WO | 01/39806 | 6/2001 |
| WO | WO 01/047552 | 7/2001 |
| WO | 01/74382 | 10/2001 |
| WO | WO 01/91807 | 12/2001 |
| WO | 02/087424 | 11/2002 |
| WO | WO 2004/069159 | 8/2004 |
| WO | WO 2004/100983 | 11/2004 |
| WO | 2004/110250 | 12/2004 |
| WO | 2005/087275 | 9/2005 |
| WO | 2006/012527 | 2/2006 |
| WO | WO 2006/034046 | 3/2006 |
| WO | WO 2006/065943 | 6/2006 |
| WO | 2006/071754 | 7/2006 |
| WO | 2006/101845 | 9/2006 |
| WO | 2007/006041 | 1/2007 |
| WO | 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | WO 2009/026177 | 2/2009 |

OTHER PUBLICATIONS

Ilgan et al., "Imaging tumor folate receptors using 111IN-DTPA-methotrexate." *Cancer Biother. Radiopharm.*, 1998, 13(3) pp. 177-184.

Akihiro H. et al., "Affinity for a-tocopherol transfer protein as a determinant of the biological activities of vitamin E analogs." *Federation of European Biochemical Societies*, 1997, vol. 409, pp. 105-108.

Kazui S. et al., "Novel vitamin D3 antipsoriatic antedrugs: 16-En-22-oxa-1a,25-(OH)2D3 analogs," *Bioorganic & Medicinal Chemistry*, 2006, vol. 14, pp. 1838-1850.

Hisashi T. et al., "c-Fos protein as a target of anti-osteoclastogenic action of vitamin D, and synthesis of new analogs," journal article, *The Journal of Clinical Investigation*, 2006, vol. 116, No. 2, February, pp. 528-535.

Masato S. et al., "Synthesis and biological activities of new 1a,25-dihydroxy-19-norvitamin D3 analogs with modifications in both the A-ring and the side chain," journal article, *Bioorganic & Medicinal Chemistry*, 2006, 14(12) pp. 4277-4294.

Agoston E.S. at al., "Vitamin D Analogs as Anti-Carcinogenic Agents" *Anti-Cancer Agents in Medicinal Chemistry* 2006, 6(1), pp. 53-71.

Lonsdale, D., "A Review of the Biochemistry, Metabolism and Clinical Benefits of Thiamin(e) and Its Derivatives." *Evidence-Based Complementary & Alternative Medicine: eCAM.* Advance Access Publication, vol. 3, Feb. 2006, pp. 49-59.

Nosaka, K. et al., "Separate Determination of Anticoccidial Thiamine Analogs by High-Performance Liquid Chromatography." *ActaA Vitaminol. Et Enzymol.*, 1984, vol. 6 92), pp. 137-142.

Kandiko, C.T. et al., "Inhibition of Rat Brain Pyruvate Dehydrogenase by Thiamine Analogs." *Biochem. Pharmacology*, vol. 37, No. 22, (1988) pp. 4375-4380.

Spry, C. et al., "A Class of Pantothenic Acid Analogs Inhibits Plasmodium Falciparum Pantothenate Kinase and Represses the Proliferation of Malaria Parasites." *Antimicrobial Agents and Chemotherapy*, Nov. 2005, pp. 4649-4657.

Sargent, D.R. et al., "Antimetabolites of Pantothenic Acid, Ureido- and Carbamoyl-Derivatives." *Texas Reports on Biology and Medicine*, 1975, vol. 33, No. 3, pp. 433-443.

Hanck, a.B. et al., "Dexpanthenol (Ro 01-4709) in the treatment of constipation." Abstract, Acta Vitaminol Enzymol, 1982, vol. 4 (1-2), pp. 87-97.

Kagechika, H. et al., "Synthetic Retinoids: Recent Developments Concerning Structure and Clinical Utility." *J. Med. Chem.*, Sep. 22, 2005, vol. 48, No. 19, pp. 5875-5883.

Shealy, Y.F. "Synthesis and Evaluation of Some New Retinoids for Cancer Chemoprevention." *Preventive Medicine*, 1989, vol. 18, pp. 624-645.

Landuer, W. et al., "The Interaction in Teratogenic Activity of the Two Niacin Analogs 3-acetylpyridine and 6-aminonicotinamide," *J Experimental Zoology*, 1962, vol. 151, pp. 253-258.

Renz, P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 5287-5291.V.

Ayers, W.A., "Effect of Vitamin B12 and Analogs on the Respiration of a Marine Bacterium." *Archives of Biochemistry and Biophysics*, 1962, vol. 96, pp. 210-215.

Toraya, T. et al., "Immobilized Derivatives of Vitamin B12 Coenzyme and Its Analogs." *Methods in Enzymology*, 1980, vol. 67, pp. 57-66.

Ueda, M. et al., "Effect of Vitamin B12 Derivatives on Urinary Excretion of Methylmalonic Acid in Liver Diseases." *Acta Med. Okayama*, 1970, vol. 24, pp. 365-372.

Toraya, T. et al., "The Synthesis of Several Immobilized Derivatives of Vitamin B12 Coenzyme and Their Use as Affinity Adsorbents for a Study of Interactions of Diol Dehydrase with the Coenzyme." *Journal of Biological Chemistry*, 1980, vol. 255, No. 8, Apr. 25, pp. 3520-3525.

Takahata, Y. et al., "Synthesis, Properties and Microbiological Activity of Hydrophobic Derivatives of Vitamin B12." *J. Nutr. Sci. Vitaminol.*, 1995, vol. 14, pp. 515-526.

Kamao, M. et al., "Determination of Plasma Vitamin K by High Performance Liquid Chromatography with Fluorescence Detection Using Vitamin K Analogs as Internal Standards." *J. of Chromatography B.*, 2005, vol. 816, pp. 41-48.

Nishikawa, Y. et al., "Growth Inhibition of Hepatoma Cells Induced by Vitamin K and Its Analogs." *Journal of Biological Chemistry*, 1995, vol. 270, No. 47, Nov. 24, pp. 28304-28310.

Mack, D.O. et al., "The Carboxylation Activity of Vitamin K Analogs with Substitutions at Position 2, 3, or 5." *Journal of Biological Chemistry*, '1979, vol. 254, Apr. 25, pp. 2656-2664.

Mock, D.M. et al., "Urinary Biotin Analogs Increase in Humans During Chronic Supplementation: the Analogs are Biotin Metabolites." *The American Physiological Society*, 1997, pp. 83-85.

International Search Report for PCT/US2002/13890 completed Oct. 28, 2002.
Vesely, D.L. et al., "Biotin Analogs Activate Guanylate Cyclase." *Molecular and Cellular Biochemistry*, 1984, vol. 60, pp. 109-114.
Lambooy, J.P., "Riboflavin Analogs Utilized for Metabolism by a *Lactobacillus casei* Mutant." *Int. J. Biochem.*, 1984, vol. 16, No. 2, pp. 231-234.
Nielsen, P. et al., "Phosphates of Riboflavin and Riboflavin Analogs: A Reinvestigation by High-Performance Liquid Chromatography." *Analytical Biochemistry*, 1983, vol. 130, pp. 359-368.
Arya, P. et al., "Design and Synthesis of Analogs of Vitamin E: Antiproliferative Activity Against Human Breast Adenocarcinoma Cells." *Bioorganic & Medicinal Chemistry Letters*, 1998, vol. 8, No. 18, pp. 2433-2438.
Trachewsky, D. "Antihypertensive Effect of Riboflavin Analogs in Rats with Mineralocorticoid-Induced Hypertension." *Hypertension*, 1981, vol. 3, No. 1, Jan.-Feb., pp. 75-80.
Skinner, W.A. et al., "Structure-Activity Relations in the Vitamin E Series. II Derivatives of alpha-Tocopherol Substituted at the 5-Methyl Group." *J Med. Chem.*, 1962, vol. 12, pp. 64-66.
Neuzil, J. et al., "Vitamin E. Analogs: A New Class of Multiple Action Agents with Anti-Neoplastic and Anti-Atherogenic Activity." *Apoptosis*, 2002, vol. 7, pp. 179-187.
Politis, I. et al., " The Effect of Various Vitamin E Derivatives on the Urokinase-Plasmogen Activator System of Ovine Macrophages and Neutrophils." *British Journal of Nutrition*, 2003, vol. 89, pp. 259-265.
Wang, X. et al., "Vitamin E Analogs Trigger Apoptosis in HER2/erbB2-Overexpressing Breast Cancer Cells by Signaling Via the Mitochondria! Pathway." *Biochemical and Biophysical Research Communication*, 2005, vol. 326, pp. 282-289.
Holladay et al., "Riboflavin-mediated delivery of a macromolecule into cultured human cells," *Biochim Biophys Acta* 1426(1): 195-204 (1999).
Kennedy et al., "Optical imaging of metastatic tumors using a folate-targeted fluorescent probe," *J. of Biomedical Optics*, vol. 8, No. 4, pp. 636-641, Oct. 2003.
Low PS, Leamon CP, Reddy JA, Green MA, Mathias C, Turk MJ, Waters DJ, Lu J, Lee RJ and Kennedy MD, "Folate-mediated delivery of therapeutic and imaging agents to cancer tissue," Gene, Drug Therapy, and Molecular Biology (Abstract), 2000.
Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues In Vivo," *International Symposium on Tumor Targeted Delivery Systems*, Bethesda, Maryland. British Journal of Pharmacology, vol. 134 (Abstract), 2001.
Kern, et al., "Evaluation of the Culprit Plaque and the Physiological Significance of Coronary Atherosclerotic Narrowings," Circulation, 2001; 103:3142-3149.
Phelps et al., Journal of Nuclear Medicine, 1975, 16(3): 210-224.
Snook et al., Br. J. Cancer, 1990, 62 (Suppl. X): 89-91.
Patton, Radiographics, 1998, 18: 995-1007.
Kanagaki et al., "Pituitary Gland and Parasellar Region," in *Magnetic Resonance Tomography*, Reiser et al. (eds.), 2008, p. 422.
Barnes, H. H., et al., "Purification of Catechol Siderophores by Boronate Affinity Chromatography: Identification of Chrysobactin From *Erwinia carotovora subsp. carotovora*", 1999, *BioMetals*, vol. 12, pp. 83-87.
Collins, Peter, et al., "Monosaccharides, Their Chemistry and Their Roles in Natural Products", 1995 *Wiley Publishers*, Book Reference, We will provide a copy of the book if requested.
Georgakoudi, Irene, et al., "In Vivo Flow Cytometry: A New Method for Enumerating Circulating Cancer Cells", Aug. 1, 2004, *Cancer Research*, No. 64, pp. 5044-5047.
Hanessian, Stephen, "Preparative Carbohydrate Chemistry", 1997 *Marcel Dekker, Inc.*, Book Reference, We will provide a copy of the book if requested.
Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.

Iijima, Masatomi, et al., "IC202A, A New Siderophore With Immunosuppressive Activity Produced by *Streptoalloteichus* sp. 1454-19. I. Taxonomy, fermentation, isolation and biological activity.", Jan. 1999, *The Journal of Antibiotics (Tokyo)*, vol. 52, No. 1, pp. 20-24.
Lingwood, Clifford A., "Oligosaccharide Receptors for Bacteria: A View to a Kill", 1998, *Curr Opin Chem Biol.*, pp. 695-700.
Michelson, Alan D., et al., "Evaluation of Platelet Function by Flow Cytometry", 2000, Methods, vol. 21, pp. 259-270.
Holmgren et al., "Strategies for the Induction of Immune Responses At Mucosal Surfaces Making Use of Cholera Toxin B Subunit As Immunogen, Carrier, and Adjuvant", Am. J. Trop Med Hyd, 50, pp. 42-54, 1994.
Novak, J., et al., "In Vivo Flow Cytometer for Real-Time Detection and Quantification of Circulating Cells", Jan. 1, 2004 *Optics Letters*, vol. 29, No. 1, pp. 77-79.
Ratledge, Colin, et al., "The Occurrence of Carboxymycobactin, The Siderophore of Pathogenic Mycobacteria, As a Second Extracellular Siderophore in *Mycobacterium smegmatis*", 1996 *Microbiology*, vol. 142, pp. 2207-2212.
Scharfman, Andree, et al., "*Pseudomonas aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.
Albrecht-Gary et al., "Bacterial Iron Transport: Coordination Properties of Pyoverdin PaA, a Peptidic Siderophore of *Pseudomonas aeruginosa*", 1994. Inorg. Chem., 33 (26), pp. 6391-6402.
Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.
Tang, Hailun, et al., "Prostate Targeting Ligands Based on $N$-Acetylated α-Linked Acidic Dipeptidase", (2003), *Biochemical and Biophysical Research Communications*, vol. 307, pp. 8-14.
Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.
Schalk, Isabelle J., et al., "Iron-Free Pyoverdin Binds to Its Outer Membrane Receptor FpvA in *Pseudomonas aeruginosa*: A New Mechanism for Membrane Iron Transport", 2001, *Molecular Microbiology*, vol. 39, No. 2, pp. 351-360.
Reddy et al., "Folate-Mediated Targeting of Therapeutic and Imaging Agents to Cancers", Critical Reviews in Ther. Drug Carrier Systems 15: 587-627, 1998.
Wiener et al., "Targeting Dendrimer-Chelates to Tumors and Tumor Cells Expressing the High-Affinity Folate Receptor," *Investigative Radiology*, 1997; 32(12):748-754.
Paulos et al., "Ligand Binding and Kinetics of Folate Receptor Recycling in Vivo: Impact on Receptor-Mediated Drug Delivery," *Molecular Pharmacology*, 2004; 66:1406-1414.
NCBI, MeSH definition for Indocarbocyanine Green, 2 pages, 2002.
Achilefu et al., "Novel Receptor-Targeted Fluorescent Contrast Agents for In Vivo Tumor Imaging", Investigative Radiology, vol. 35, No. 8, pp. 479-485, Aug. 2000.
Antohe et al., "Increased uptake of folate conjugates by activated macrophages in experimental hyperlipemia", Cell Tissue Research, vol. 320, No. 2, pp. 277-285, May 2005.
Aviram et al., "Intralipid infusion abolishes ability of human serum to cholesterol-load cultured macrophages", Arteriosclerosis, vol. 9, pp. 67-75, 1989.
Ballou et al., "Tumor labeling in vivo using cyanine-conjugated monoclonal antibodies", Cancer Immunol Immunother, vol. 41, pp. 257-263, 1995.
Barrera et al., "Synovial macrophage depletion with clodronate-containing liposomes in rheumatoid arthritis", Arthritis and Reheumatism, vol. 43, pp. 1951-1959, Sep. 2000.
Beaumont et al., "Selective Fluorodenitration of Chloronitroaromatics", J. Fluorine Chem., vol. 63, pp. 25-30, 1993.
U.S. Appl. No. 13/463,447, filed May 3, 2012, Low et al.
Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.

Bettio et al., "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.

Boechat et al., "Fluorodenitrations Using Tetramethylammonium Fluoride", J. Soc. Chem, Commun., pp. 921-992, 1993.

Boente et al., "Screening, imaging, and Early Diagnosis of Ovarian Cancer", Clinical Obstetrics and Gynecology, vol. 37, No. 2, pp. 377-391, Jun. 1994.

Bonasera et al., "The Synthesis of [26, 27-11C]Dihydroxyvitamin D3, a Tracer for Positron Emission Tomography (PET), Bioorganic & Medicinal Chemistry", Elsevier Science Ltd., vol. 9, pp. 3123-3128, 2001.

Burke et al., "Book Review. The Macrophage", British Journal of Cancer, vol. 89, p. 421, 2003.

Campbell et al., "Folate-binding Protein is a Marker for Ovarian Cancer", Cancer Research, vol. 51, pp. 5329-5338, Oct. 1, 1991.

Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.

Reddy et al., "Folate receptor specific anti-tumor activity of folate-mitomycin conjugates", Cancer Chemother. Pharmacol., 58(2): 229-36, 2006.

Case, "Ultrasound Physics and Instrumentation", Surgical Clinics of North America, vol. 78, No. 2, pp. 197-217, Apr. 1998.

Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.

Tung et al., "Preparation of a Cathepsin D Sensitive Near-Infrared Fluorescence Probe for Imaging", American Chemical Society, vol. 10, No. 5, pp. 692-696, Sep. 20, 1999.

Cohen et al., "Screening for ovarian cancer: The role of noninvasive imaging techniques", Am J. Obstet Gynecol., vol. 170, No. 4, pp. 1088-1094, 1994.

Cohen et al., "Three-Dimensional Power Doppler Ultrasound Improves the Diagnostic Accuracy for Ovarian Cancer Prediction", Gynecologic Oncology, vol. 82, pp. 40-48, 2001.

Cox et al., "Anhydrous, Tetrabutylammonium Fluoride: A Mild but Highly Efficient Source of Nucleophilic Fluoride Ion", J. Org. Chem., No. 49, pp. 3216-3219, Feb. 8, 1984.

Degrado et al., "Synthesis and Evaluation of (18)F-Labeled Choline Analogs as Oncologic PET Tracers", J. Nuclear Medicine, vol. 42, No. 12, pp. 1805-1814, 2001.

DePriest et al., "Transvaginal Sonography as a Screening Method for the Detection of Early Ovarian Cancer", Gynecologic Oncology, vol. 65, No. GO974705, pp. 408-414, 1997.

Forstner et al., "CT and MRI of ovarian cancer", Abdominal Imaging, vol. 20, pp. 2-8, 1995.

Garg et al., "Fluorine-18 Labeling of Monoclonal Antibodies and Fragments with Preservation of Immunoreactivity", Bioconjugate Chem., vol. 2, No. 1, pp. 44-49, 1991.

Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.

Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, 1972.

Greenman et al., "Heterogeneous Expression of Two Somatostatin Receptor Subtypes in Pituitary Tumors," Journal of Clinical Endocrinology and Metabolism, vol. 78, No. 2, pp. 398-403, 1994.

Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.

Harris et al., "Human leukemic models of myelomonocytic development: a review of the HL-60 and U937 cell lines", Journal of Leukocyte Biology, vol. 37., No. 4, pp. 407-422, 1985.

Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.

Johnstrom et al.,"18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.

Karlan, "The Status of Ultrasound and Color Doppler Imaging for the Early Detection of Ovarian Cancer", Cancer Investigation, vol. 15, No. 3, pp. 265-269, 1997.

Karlan et al., "Ovarian Cancer Screening: The Role of Ultrasound in Early Detection", Cancer Supplement, vol. 76, No. 10, pp. 2011-2015, Nov. 15, 1995.

Kennedy et al., "Evaluation of Folate Conjugate Uptake and Transport by the Choroid Plexus of Mice", Pharmaceutical Research, vol. 20, No. 5, p. 714-719, May 2003.

Kennedy et al., "Optical imaging of metastatic tumors using a folate-targeted fluorescent probe", J. of Biomedical Optics, vol. 8, No. 4, pp. 636-641, Oct. 2003.

Kinne et al., "Macrophage in rheumatoid arthritis", Arthritis Research, vol. 2, No. 3, pp. 189-202, 2000.

Konda et al., "Development of a Tumor-Targeting MR Contrast Agent Using the High-Affinity Folate Receptor", Investigative Radiology, vol. 35, No. 1, pp. 50-57, 2000.

Kramer, "Basic Principles of Magnetic Resonance Imaging", Radiological Clinics of North America, vol. 22, No. 4, pp. 765-778, Dec. 1984.

Kuriowa et al., "Development of a Fluorescein Operative Microscope for Use During Malignant Glioma Surgery", Elsevier Science Inc., vol. 50, pp. 41-49, 1998.

Leamon et al., "Folate-mediated targeting: from diagnosis to drug and gene therapy" DDT vol. 6 No. 1 44-51, Jan. 2001.

Leamon et al., "Synthesis and Biological Evaluation of EC140: A Novel Folate—Targeted Cinca Alkaloid Conjugate", Bioconjugate Chem., vol. 17, No. 5, pp. 1226-1232, 2006.

Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.

Licha et al., "Hydrophilic Cyanine Dyes as Contrast Agents for Near-infrared Tumor Imaging: Synthesis, Photophysical Properties and Spectroscopic in vivo Characterization, Photochemistry and Photobiology", vol. 72, No. 3, pp. 392-398, 2000.

Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.

Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.

Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.

Mahmood et al., "Near Infrared Optical Imaging for Protease Activity for Tumor Detection", Radiology, 213:866-870, 1999.

Maiman et al., "Laproscopic Excision of Ovarian Neoplasm Subsequently Found to Be Malignant", Obstetrics & Gynecology, vol. 77, No. 4, pp. 563-565, Apr. 1991.

Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.

Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, vol. 30A, No. 3, pp. 363-369, 1994.

Mathias et al.,"Preparation of 66Ga- and 68GA-labeled GA(III)-deferoxamine-folate as potential folate-receptor-targeted PET radiopharmaceuticals", Nuclear Medicine and Biology, vol. 30, pp. 725-731, 2003.

Mulherin et al., "Synovial tissue macrophage populations and articular damage in rheumatoid arthritis", Arthritis and Rheumatism, vol. 39, No. 1, pp. 115-124, 1996.

Murakami et al., "18F-Labelled Annexin V: A PET Tracer for Apoptosis Imaging", European Journal of Nuclear Medicine and Molecular Imaging, vol. 31, No. 4, pp. 469-474, 2004.

Nagayoshi et al., "Arthritis and Reheumatism", vol. 52, pp. 2666-2675, Sep. 9, 2005.

Nezhat et al., "Four ovarian cancers diagnosised during laproscopic management of 1011 women with adnexal masses", Am J Obstet Gynecol., vol. 167, No. 3, pp. 790-796, 1992.

Olma et al., "4-[18F]fluorophenyl ureas via carbamate-4-nitrophenyl esters and 4-[18F]Fluoroaniline", Journal of Labeled Compd. and Radiopnarm, vol. 49, pp. 1037-1050, 2006.

Paigen et al., "Variation in susceptibility to atherosclerosis among inbred strains of mice", Atherosclerosis, vol. 57, No. 1, pp. 65-73, 1985.

Pasterkamp et al., "Techniques characterizing the coronary atherosclerotic plaque: Influence on clinical decision making?", J. Amer. Coll. Cardiol. 36:13-21, 2000.

Paulos et al., "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.

Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.

Rampone et al., "Ovarian cancer screening by transvaginal color Doppler ultrasonography", Minerva Ginecologica, vol. 53, Suppl. 1 al N 1, pp. 125-128, 2001.

Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.

Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.

Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.

Sato et al., "Usefulness of Mass Screening for Ovarian Carcinoma Using Transvaginal Ultasonography", American Cancer Society, vol. 89, No. 3, pp. 582-588, 2000.

Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.

Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Feb. 2000.

Shoup et al., "Synthesis of Fluorine-18-Labeled Biotin Derivatives: Biodistribution and Infection Localization", J. Nuclear Medicine, vol. 35, No. 10, pp. 1685-1690, 1994.

Sijtsema et al., "Confocal Direct Imaging Raman Microscope: Design and Application in Biology", Applied Spectroscopy, vol. 52, Issue 3, pp. 348-355, 1998.

Sima et al., "Experimental obstructive coronary atherosclerosis in the hyperlipidemic hamster", J Submicrosc Cytol Pathol, vol. 22, No. 1, pp. 1-16, 1990.

Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 1990.

Smart et al., "Protein kinase C activators inhibit receptor-mediated potocytosis by preventing internalization of caveolae", Journal of Cell Biology, vol. 124, No. 3, pp. 307-313, 1994.

Solomon et al., "Computerized Tomography in Ovarian Cancer", Gynecologic Oncology, vol. 15 pp. 48-55, 1983.

Sun et al., "Anhydrous Tetrabutylammonium Fluoride", J. Am. Chem. Soc., vol. 127, No. 7, pp. 2050-2051, 2005.

Sun et al., "Room-Temperature Nucleophilic Aromatic Fluorination: Experimental and Theoretical Studies", Angew. Chem. Int. Ed., No. 45, pp. 2720-2725, 2006.

Sundstrum et al., "Establishment and characterization of a human histiocytic lymphoma cell line (U-937)", International Journal of Cancer, vol. 17, No. 5, pp. 565-577, 1976.

Sutcliffe-Goulden, "Solid Phase Synthesis of [18F]Labelled Peptides for Positron Emission Tomography", Bio. & Medicin. Chem. Letters, No. 10, pp. 1501-1503, 2000.

Tan et al., "A Complete Remote-Control System for Reliable Preparation of [18F]altanserin", Applied Radiation and Isotopes, vol. 50, pp. 923-927, 1999.

Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.

Toffoli et al., "Overexpression of Folate Binding Protein in Ovarian Cancers", Int. J. Cancer (Pred. Oncol.), vol. 74, pp. 193-198, 1997.

Urban, "Screening for ovarian cancer: We now need a definitive randomized trial", BMJ, vol. 319, pp. 1317-1318, Nov. 20, 1999.

Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.

Wang et al., Chemokines and their role in cardiovascular diseases, TCM, vol. 8, pp. 169-174, 1998.

Weissleder et al., "In vivo imaging of tumors with protease-activated near-infrared fluorescent probes", Nature Biotechnology, vol. 17, pp. 375-378, 1999.

Weitman et al., "The folate receptor in central nervous system malignancies of childhood", Journal of Neuro-Oncology, vol. 21, pp. 107-112, 1994.

Whitehurst et al., "Development of an alternative light source to lasers for biomedical applications", SPIE, vol. 2629, pp. 291-298, 1993.

Wu et al., "Expression of Folate Receptor Type A in Relation to Cell Type Malignancy, and Differentiation in Ovary, Uterus and Cervix", Cancer Epidemiology, Biomarkers & Prevention, vol. 8, pp. 775-782, Sep. 1999.

Yavorsky et al., Antiparticles:, Handbook on Physics, pp. 339-340, 1984.

Zeisel et al., "Choline, an Essential Nutrient for Humans", The Faseb Journal, vol. 5, No. 7, pp. 2093-2098, 1991.

Delaloye et al., "Tumor imaging with monoclonal antibodies", Seminars in Nuclear Medicine, 25:144-164, 1995.

Reubi, "The role of peptides and their receptors as tumor markers", Endocrinology & Metabolism Clinics of North America, 22: 917-939, 1993.

Garin-Chesa et al., "Trophoblast and ovarian cancer antigen LK26. Sensitivity and specificity in immunopathology and molecular identification as a folate-binding protein", American Journal of Pathology, 142: 557-567, 1993.

Patrick et al., "Folate receptors as potential therapeutic targets in choroid plexus tumors of SV40 transgenic mice", Journal of Neuro-Oncology, 32: 111-123, 1997.

Weitman et al., "Distribution of the folate receptor GP38 in normal and malignant cell lines and tissues", Cancer Research, 52: 3396-3401, 1992.

Mathias et al., "Indium-111-DTPA-folate as a potential folate-receptor-targeted radiopharmaceutical", Journal of Nuclear Medicine, 39: 1579-1585, 1998.

Acosta et al., "Chromoendoscopy—where is it useful?", Journal of Clinical Gastroenterology, 27:13-20,1998.

Fleischer, "Chromoendoscopy and magnification endoscopy in the colon", Gastrointestinal Endoscopy, 49: S45-49, 1999.

Stepp et al., "Fluorescence endoscopy of gastrointestinal diseases: basic principles, techniques, and clinical experience", Endoscopy, 30: 379-386, 1998.

Ballou et al., "Tumor detection and visualization using cyanine fluorochrome-labeled antibodies", Biotechnology Progress, 13: 649-658, 1997.

Licha et al., "Synthesis, characterization, and biological properties of cyanine-labeled somatostatin analogues as receptor-targeted fluorescent probes", Bioconjugate Chemistry, 12: 44-50, 2001.

Becker et al., "Receptor-targeted optical imaging of tumors with near-infrared fluorescent ligands", Nature Biotechnology, 19: 327-331, 2001.

Terpetschnig et al., "Synthesis of squaraine-N-hydroxysuccinimide esters and their biological application as long-wavelength fluorescent labels", Analytical Biochemistry, 217: 197-204, 1994.

Mujumdar et al., "Cyanine dye labeling reagents containing isothiocyanate groups", Cytometry, 10: 11-19, 1989.

Wang et al., "Design and synthesis of [111In]DTPA-folate for use as a tumor-targeted radiopharmaceutical", Bioconjugate Chemistry, 8: 673-679, 1997.

Dimartino et al., "Antiarthritic and immunoregulatory activity of spirogermanium", Journal of Pharmacology an Experimental Therapeutics, 236: 103-110, 1986.

Ross et al., "Differential regulation of folate receptor isoforms in normal and malignant tissues in vivo and in established cell lines. Physiologic and clinical implications", Cancer, 73: 2432-2443, 1994.

Ross et al., "Folate receptor type beta is a neutrophilic lineage marker and is differentially expressed in myeloid leukemia", Cancer, 85: 348-357, 1999.

Curtin et al., "Stage IV ovarian cancer: impact of surgical debulking", Gynecologic Oncology, 64: 9-12, 1997.

Munkarah et al., "Prognostic significance of residual disease in patients with stage IV epithelial ovarian cancer", Gynecologic Oncology, 64: 13-17, 1997.

Murolo et al., "Ultrasound examination in ovarian cancer patients. A comparison with second look laparotomy", Journal of Ultrasound in Medicine, 8: 441-443, 1989.

Piver et al., "Second-look laparoscopy prior to proposed second-look parotomy", Obstetrics and Gynecology, 55: 571, 1980.

Bell et al., "Intraoperative radioimmunodetection of ovarian cancer using monoclonal antibody B72.3 and a portable gamma-detecting probe", Obstetrics and Gynecology, 76: 607-677, 1990.

Reuter et al., "Detection of colorectal carcinomas by intraoperative RIS in addition to preoperative Ris: surgical and immunohistochemical findings", European Journal of Nuclear Medicine, 19: 102-109, 1992.

Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.

Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.

Folli et al., "Antibody-indocyanin conjugates for immunophotodetection of human squamous cell carcinoma in nude mice", Cancer Research, 54: 2643-2649, 1994.

Bannwarth et al., "Methotrexate in rheumatoid arthritis. An update", Drugs, 47: 25-50, 1994.

Thomas F. Budinger et al., "New Approaches to Targeting Arthritis with Radiopharmaceuticals, " The Journal of Rheumatology 1995, pp. 62-67, vol. 22:1 Supplement.

"Osteomyelitis", XP-002569963, URL:http://emedicine.medscape.com/article/785020-overview>, retrieved Feb. 22, 2010.

Marecos et al., "Antibody-Mediated versus Nontargeted Delivery in a Human Small Cell Lung Carcinoma Model", Bioconjugate Chemistry, 9:184-191 (1998).

He et al., "In vivo quantitation of rare circulating tumor cells by multiphoton intravital flow cytometry," Proc Nat Acad Sci USA, 2007; 104: 11760-11765.

Chen et al., "In vivo imaging of proteolytic activity in atherosclerosis," Circulation, 2002, 105: 2766-2771.

Bettegowda, et al., Proc. Natl. Acad. ScL U.S.A., 102: 1145-1150, 2005.

Bunce, et al., Infect. Immun., 60: 2636-2640, 1992.

Claassen E. et al., "Preparation and characteristics of dichloromethylene diphosphonate-containing liposomes," J. Microencapsul., 3: 109-14, 1986.

Marceau et al., Bioorganics and Medical Chemistry Letters, 15(24): 5442-5445, 2005.

Novabiochem® Letters, "Resins for the synthesis of biotinylated and fluorescently-labeled peptides," Jan. 2004, pp. 1-4, 2004.

Novabiochem® Letters, "Products for peptide ligation," Feb. 2004, pp. 1-4, 2004.

Novabiochem® Letters, "Amino acids for Fmoc SPPS," Mar. 2004, pp. 1-4, 2004.

Novabiochem® Letters, "PEG reagents," Apr. 2004, pp. 1-4, 2004.

Massoud et al., "Molecular imaging in living subjects: seeing fundamental biological processes in a new light", 2003, Genes Dev. 17: 545-580.

Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.

Leamon et al., "Folate-mediated Drug Delivery: Effect of Alternative conjugate Chemistry", Journal of Drug Targeting, Col. 7, No. 3, 157-169, 1999.

Cochlovius, "Therapeutic Antibodies", Modern Drug Discovery, pp. 33-38, 2003.

Feldman M. et al., "Anti-TNFα therapy is useful in rheumatoid arthritis and Crohn's disease: analysis of the mechanism of action predicts utility in other diseases," *Transplant. Proc.*, 1998, 30, pp. 4126-4127.

Leamon, C.P. et al., "Synthesis and biological evaluation of EC20: A new folate-derived, 99mTc-based radiopharmaceutical", *Bioconjugate Chemistry*, vol. 13, No. 6, pp. 1200-1210, XP002284075, 1995.

Leamon et al., "Selective Targeting of Malignant Cells with Cytotoxin-Folate Conjugates," *J. Drug Targeting*, 2: 101-112 (1994).

Lu et al., "Folate-Targeted Enzyme Prodrug Cancer Therapy Utilizing Penicillin-V Amidase and a Doxorubicin Prodrug," *J. Drug Targeting*, 7: 43-53 (1999).

Mestas J. et al, "Of mice and not men: differences between mouse and human immunology," *J. of Immunology*, 2004, 172, pp. 2731-2738.

Caliceti et al., "Pharmacokinetic and biodistibution properties of poly9ethylene glycol)â∈protein conjugates", 2003, Adv. Drug Del. Rev. 55: 1261-1277.

Nakashima-Matsushita et al., "Selective Expression of Folate Receptor β and its Possible Role in Methotrexate Transport in Synovial Macrophages from Patients with Rheumatoid Arthritis," *Arthritis Rheum.* 42(8): 1609-1616 (1999).

Reddy et al., "Optimization of Folate-Conjugated Liposomal Vectors for Folate Receptor-Mediated Gene Therapy," *J. Pharm. Sciences*, 88: 1112-1118 (1999).

Sudimack et al., "Targeted Drug Delivery via the Folate Receptor," *Adv. Drug Delivery Reviews*, 41: 147-162 (2000).

Turk, M.J. et al., "Folate-targeted imaging of activated macrophages in rats with adjuvant-induced arthritis," *Arthritis and Rheumatism*, 2002, vol. 46, No. 7, pp. 1947-1955, XP002284074.

Van Noort J.M. et al., "Cell biology of autoimmune diseases," *International Review of Cytology*, 1998, 178, pp. 127-204.

Westerhof G.R. et al., "Carrier- and Receptor-Mediated Transport of Folate Antagonists Targeting Folate-Dependent Enzymes: Correlates of Molecular-Structure and Biological Activity," Molecular Pharmacology, 1995, 48, pp. 459-471.

Eugene C. Roberts and Y. Fulmer Shealy, "Folic Acid Analogs. Modifications in the Benzene-Ring Region. 3. Neohomofolic and Neobishomofolic Acids. An Improved Synthesis of Folic Acid and Its Analogs.," Journal of Medicinal Chemistry, 1973, vol. 16, No. 6, pp. 697-699.

Tamaki et al., "PET in Oncology", Jpn J Cancer Clin, 2003, 49(6): 531-535.

Remington: The Science & Practice of Pharmacy, 21th Edition (Lippincott Williams & Wilkins, 2005) (Book Reference-Applicant will provide a copy of the book if requested).

Eugene C. Roberts and Y. Fulmer Shealy, "Folic Acid Analogs. Modifications in the Benzene-Ring Region. 2. Thiazole Analogs," Journal of Medicinal Chemistry, 1972, vol. 15, No. 12, pp. 1310-1312.

Eugene C. Roberts and Y. Fulmer Shealy, "Folic Acid Analogs. Modifications in the Benzene-Ring Region. 1.2'- and 3'- Azafolic Acids," Journal of Medicinal Chemistry, 1971, vol. 14, No. 2, pp. 125-130.

Louis T. Weinstock, Bernard F. Grabowski, and C. C. Cheng, "Folic Acid Analogs. II. p-{[2,6-Diamino-8-purinyl)methyl]amino}-benzoyl-L-glutamic Acid and Related Compounds," Journal of Medicinal Chemistry, 1970, vol. 13, No. 5, pp. 995-997.

Lothar Bock, George H. Miller, Klaus-J. Schaper, and Joachim K. Seydel, "Sulfonamide Structure-Activity Relationships in a Cell-Free System. 2. Proof for the Formation of a Sulfonamide-Containing Folate Analog.," Journal of Medicinal Chemistry, 1974, vol. 17, No. 1, pp. 23-28.
Eugene C. Roberts and Y. Fulmer Shealy, "Folic Acid Analogs. Modifications in the Benzene-Ring Region. 4. 3'-Ethyl- and 3'-Isopropylfolic Acids," Journal of Medicinal Chemistry, 1974, vol. 17, No. 2, pp. 219-222.
William W. Lee, Abelardo P. Martinez, and Leon Goodman, "Folic Acid Antagonists. Methotrexate Analogs Containing Spurious Amino Acids. Dichlorohomofolic Acid.", Journal of Medicinal Chemistry, 1974, vol. 17, No. 3, pp. 326-330.
Y. H. Kim, Y. Gaumont, R. L. Kisliuk, and H. G. Mautner, "Synthesis and Biological Activity of 10-Thia-10-deaza Analogs of Folic Acid, Pteroic Acid, and Related Compounds," Journal of Medicinal Chemistry, 1975, vol. 18, No. 8, pp. 776-780.
Bendele et al., "Animal Models of Arthritis: Relevance to Human Disease", Toxicology Pathology, vol. 27, No. 1, pp. 134-142, 1999.
Nair M.G. et al., "Folate Analogues Altered in the C9-N10 Bridge Region. 10-Oxafolic Acid and 10-Oxaaminopterin, " Journal of Medicinal Chemistry, 1976, vol. 19, No. 6, pp. 825-829.
Plante L.T. et al., "Polyglutamyl and Polylysyl Derivatives of the Lysine Analogues of Folic Acid and Homofolic Acid," Journal of Medicinal Chemistry, 1976, vol. 19, No. 11, pp. 1295-1299.
Hynes J.B. et al., "Quinazolines as Inhibitors of Dihydrofolate Reductase. 4. Classical Analogues of Folic and Isofolic Acids," Journal of Medicinal Chemistry, 1977, vol. 20, No. 4, pp. 588-591.
Oatis J.E. et al., "Synthesis of Quinazoline Analogues of Folic Acid Modified at Position 10," Journal of Medicinal Chemistry, 1977, vol. 20, No. 11, pp. 1393-1396.
Nair M.G. et al., "Folate Analogues Altered in the C9-N10 Bridge Region: N10-Tosylisohomofolic Acid and N10-Tosylisohomoaminopterin," Journal of Medicinal Chemistry, 1978, vol. 21, No. 7, pp. 673-677.
Nair M.G. et al., "Folate Analogues Altered in the C9-N10 Bridge Region: 11-Thiohomofolic Acid," Journal of Medicinal Chemistry, 1979, vol. 22, No. 7, pp. 850-855.
Nair M.G. et al., "Folate Analogues Altered in the C9-N10 Bridge Region. 14. 11-Oxahomofolic Acid, a Potential Antitumor Agent," J. Med. Chem., 1980, vol. 23, pp. 59-65.
Nair M.G. et al., "Folate Analogues Altered in the C9-N10 Bridge Region. 18. Synthesis and Antitumor Evaluation of 11-Oxahomoaminopterin and Related Compounds," J. Med. Chem., 1981, vol. 24, pp. 1068-1073.

Temple Jr., C.T. et al., "Synthesis of Pseudo Cofactor Analogues as Potential Inhibitors of the Folate Enzymes," J. Med. Chem., 1982, vol. 25, pp. 161-166.
Nair M.G. et al., "Folate Analogues. 20. Synthesis and Antifolate Activity of 1', 2', 3', 4', 5', 6'-Hexahydrohomofolic Acid," J. Med. Chem., 1983, vol. 26, pp. 135-140.
Nair M.G. et al., "Folate Analogues. 21. Synthesis and Antifolate and Antitumor Activities of N10-(Cyanomethyl)-5,8- dideazafolic Acid," J. Med. Chem., 1983, vol. 26, pp. 605-607.
Nair M.G. et al., "Folate Analogues. 22. Synthesis and Biological Evaluation of Two Analogues of Dihydrofolic Acid Possessing a 7,8-Dihydro-8-oxapterin Ring System," J. Med. Chem., 1983, vol. 26, pp. 1164-1168.
Karsten M. and J. Roos, "Towards Usage-based Accounting: Applying Policy-based Intelligent Agents," ITC 15. Elsevier Science B.V., Ramaswami V. et al., eds., pp. 633-642 (1997).
Wang et al. "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996.
Matsuyama, T. et al., "Clinical significance of the folate receptor beta expression in rheumatoid synovial macrophages," Rheumatoid, Japan, Japan College of Rheumatology, 2001, vol. 41, No. 2, p. 265.
Gotoh M., "Causes and treatment of rheumatoid arthritis; recent trend I. Progress in pathogenesis of rheumatoid arthritis; role of macrophages and dendritic cells," Pharma Medica, Japan, Medical Review Co., Ltd., Tokyo, 1999, vol. 17, No. 10, pp. 35-39.
Matsuyama T. et al., "Activation and pathological significance of macrophages in rheumatoid synovitis," Clinical Immunity, Japan, Kagaku Hyoronsha, Tokyo, 1998, vol. 30, No. 2, pp. 214-219.
Mukasa A. et al., "Functional analysis of folate receptor-β in RA synovial macrophage-like cells," Rheumatoid, Japan, Japan College of Rheumatology, 2000, vol. 40, No. 2, p. 378.
Translation Document containing English translations for Gotoh (1999), Matsuyama (1998), and Mukasa (2000).
"Macrophages" from Wikipedia, available at http://en.wikipedia.org/wiki/Macrophages, 2000.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & In Vivo Studies with α-and γ-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.

Increased uptake of folate-targeted imaging agent was seen in patient with inflamed joint Fig. 8 Folate-linked chelator EC20

DIAGNOSIS OF MACROPHAGE MEDIATED DISEASE

CROSS REFERENCE TO RELATED APPLICATIONS

This application is a continuation of U.S. application Ser. No. 11/648,223, filed Dec. 29, 2006 now abandoned, which is a divisional of U.S. application Ser. No. 10/138,275, filed May 2, 2002 (now U.S. Pat. No. 7,740,854, issued Jun. 22, 2010), which claims priority under 35 U.S.C §119(e) to U.S. Provisional Application Ser. No. 60/288,208, filed on May 2, 2001.

FIELD OF THE INVENTION

This invention relates to methods for treating and monitoring disease states mediated by activated macrophages. More particularly, ligands that bind to activated macrophages are complexed with an imaging agent, or an immunogen, a cytotoxin or an agent for altering macrophage function for administration to a diseased host for diagnosis and/or treatment of macrophage mediated disease.

BACKGROUND AND SUMMARY OF THE INVENTION

The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease often resulting in organ transplant rejection.

Macrophages are generally the first cells to encounter foreign pathogens, and accordingly, they play an important role in the immune response. However, activated macrophages can contribute to the pathophysiology of disease in some instances. Activated macrophages nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response.

Rheumatoid arthritis (RA) is a systemic disease characterized by chronic inflammatory synovitis, usually involving peripheral joints. The synovial inflammation causes cartilage deterioration and bone erosion with consequent destruction of joint integrity. Rheumatoid factors, which are autoantibodies reactive with the Fc region of IgG, are found in more than two-thirds of patients with RA indicating that RA has an autoimmune component.

RA is seen throughout the world in as much as 2% of the population, with 80% of RA patients developing the disease between the ages of 35 and 50. The clinical manifestations of RA include pain, swelling, and tenderness in the joints resulting in limitation of motion, weakness, fatigue, and weight loss. RA is a systemic disease and, consequently, has extra-articular manifestations, especially in patients with high titers of rheumatoid factors. These symptoms include rheumatoid nodules with an inner zone of necrotic material, a mid-zone of macrophages, and an outer zone of granulated tissue, muscle atrophy, osteoporosis, pulmonary fibrosis, and rheumatoid vasculitis which may result in cutaneous ulceration, digital gangrene, or neurovascular disease.

Rheumatoid synovitis, characteristic of RA, results in an increase in the number of synovial lining cells, hyperplasia and hypertrophy of the synovial lining cells, microvascular injury, edema, and infiltration of cells such as T cells, macrophages, and dendritic cells. The rheumatoid synovium is characterized by the presence of secreted products of immune cells such as factors secreted by T lymphocytes including IL-2, IFN-δ, IL-6, IL-10, GM-CSF and TGFα and β and factors secreted by activated macrophages including IL-1, IL-6, IL-8, IL-10, GM-CSF, macrophage CSF, and TGFβ. The production of these cytokines appears to account for much of the pathology of RA including inflammation of the synovium, synovial cell proliferation, cartilage and bone deterioration, and systemic symptoms of the disease.

RA may be treated using various therapies including physical therapy, rest, and splinting. Therapeutic agents are also used for the treatment of RA including aspirin and nonsteroidal anti-inflammatory drugs to control local inflammation. However, these agents have a minimal effect on the progression of the disease and are associated with toxic side effects. Disease-modifying anti-rheumatic drugs, such as α-penicillamine and sulfasalazine, are also used to treat RA, but the benefit from these drugs is delayed for weeks or months and these drugs have toxic side effects. Immunosuppressive and cytotoxic drugs suppress symptoms of RA in some patients, but are associated with toxicity. Intra-articular glucocorticoids have also been used, but provide only transient relief. Accordingly, there is a need for the development of new therapies with reduced toxicity that are efficacious for the treatment of RA and other diseases caused or worsened by activated macrophages.

The folate receptor (FR) is a 38 KDa GPI-anchored protein that binds the vitamin folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not alter the vitamin's ability to bind the folate receptor, and therefore, folate-drug conjugates can readily enter cells by receptor-mediated endocytosis.

Because most cells use an unrelated reduced folate carrier (RFC) to acquire the necessary folic acid, expression of the folate receptor is restricted to a few cell types. With the exception of kidney and placenta, normal tissues express low or nondetectable levels of FR. However, many malignant tissues, including ovarian, breast, bronchial, and brain cancers express significantly elevated levels of the receptor. In fact, it is estimated that 95% of all ovarian carcinomas overexpress the folate receptor. It has recently been reported that $FR_\beta$, the nonepithelial isoform of the folate receptor, is expressed on activated (but not resting) synovial macrophages. Thus, Applicants have attempted to utilize folate-linked compounds potentially capable of altering the function of activated macrophages, to treat macrophage-mediated disease states. For example, Applicants have found that folate-linked immunogens can be used to redirect the host immune response in arthritic animals to activated macrophages at the site of inflammation to deplete macrophages and reduce arthritic inflammation.

Scintigraphic imaging agents are a million times more sensitive than magnetic resonance imaging (MRI) contrast agents, and their selectivity can be enhanced by their targeting to lesion-specific cell markers. Indeed, the radioisotope $^{99m}$Tc has been delivered to arthritic tissues using nonspecific IgG, anti-CD4 antibodies, CD11b/CD14-glycolipopeptide ligands, and E-selectin binding peptides. Preclinical studies with such radioimaging agents have clearly emphasized the value of imaging arthritic tissues in-vivo, however, the selectively of the current imaging agents is not yet optimal, and none of the present compounds is targeted exclusively to activated macrophages. In view of the emergence of folate receptor activity during macrophage activation, Applicants have undertaken to determine whether a folate-targeted $^{99m}$Tc imaging agent might be used to image arthritic lesions in vivo.

To determine whether expression of this high affinity FR might be exploited to selectively target drugs to activated macrophages at sites of inflammation, folic acid has been conjugated to a $^{99m}$Tc chelator, and its distribution evaluated in both normal and diseased tissues of rats with adjuvant-induced arthritis. The folate-linked $^{99m}$Tc chelate complex, termed EC20, was indeed found to concentrate in the arthritic extremities of diseased rats, but not in the joints of healthy rats. The intensity of the gamma scintigraphic images of affected tissues was found to be greatly reduced in the presence of excess competing folic acid. Furthermore, liver and spleen of arthritic animals also showed enhanced uptake of EC20 and increased levels of FR, confirming that systemic activation of macrophages accompanies adjuvant-induced arthritis. Depletion of macrophages from arthritic animals reduced tissue FR content and concomitantly abolished uptake of EC20. Furthermore, Kupffer cells isolated from rats with adjuvant-induced arthritis exhibited a significantly higher binding capacity for folate conjugates than Kupffer cells from healthy rats. Thus, Applicants have found that EC20 is useful for assaying the participation of activated macrophages in inflammatory pathologies such as rheumatoid arthritis.

The present invention is directed to a method for treating and monitoring disease states mediated by activated macrophages. In accordance with one embodiment of the present invention, disease states mediated by activated macrophages are treated by redirecting host immune responses to activated macrophages or by altering the function of activated macrophages or by direct killing of activated macrophages. In one aspect of the invention, to promote killing of activated macrophages, ligands that bind specifically to activated macrophages are conjugated with an immunogen to redirect host immune responses to the activated macrophage population, or they are conjugated to a cytotoxin for direct killing of macrophages. Ligands that can be used in the conjugates of the present invention include those that bind to receptors expressed specifically on activated macrophages, such as the folate receptor, or ligands such as monoclonal antibodies directed to cell surface markers specifically expressed on activated macrophages. In another aspect of the invention ligands that bind specifically to activated macrophages are conjugated with an imaging agent; the conjugate is administered to a patient for diagnosing and monitoring the progression of diseases mediated by activated macrophages.

In one embodiment, a method of treating or monitoring/diagnosing a disease state mediated by activated macrophages is provided. The method comprises the step of administering to a patient suffering from a macrophage mediated disease state an effective amount of a composition comprising a conjugate or complex of the general formula $A_b$-X, where the group $A_b$ comprises a ligand capable of binding to activated macrophages, and when the conjugate is being used for treatment of the disease state, the group X comprises an immunogen, a cytotoxin, or a compound capable of altering macrophage function, and when the conjugate is being used for monitoring/diagnosing the disease state, X comprises an imaging agent.

DETAILED DESCRIPTION OF THE INVENTION

Figure 1:
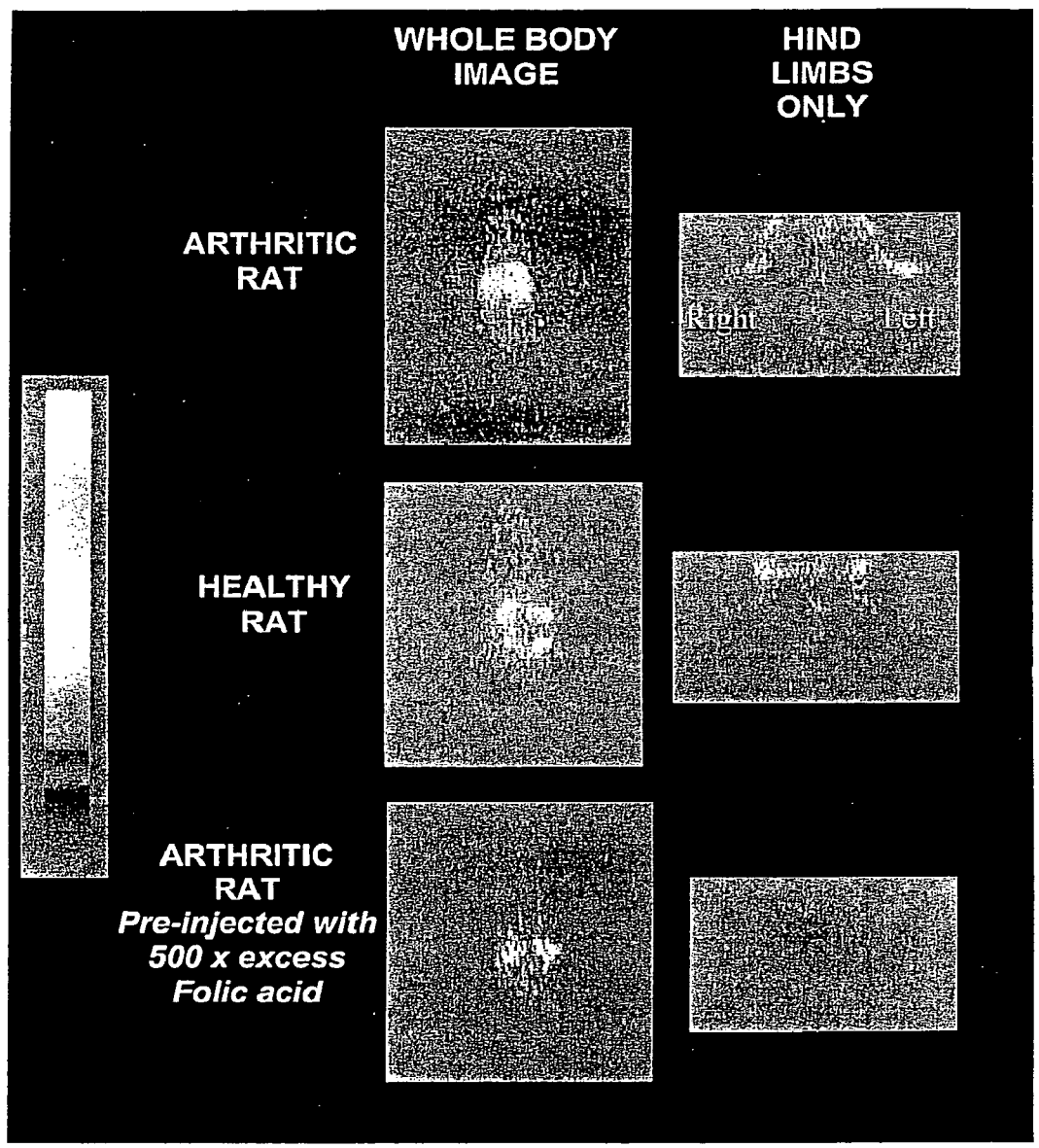
FIG. 1 shows folate-targeted imaging of arthritic rats (whole body scintigraphic images).

Methods are provided in accordance with the present invention for either treating or monitoring/diagnosing a disease state mediated by activated macrophages. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Such disease states can be monitored by first administering to a patient suffering from such disease state an effective amount of a composition comprising a conjugate of the general formula $A_b$-X wherein the group $A_b$ comprises a ligand capable of binding to activated macrophages, and the group X comprises an imaging agent and thereafter scanning the patient with an imaging device capable of detecting the imaging agent. Macrophage mediated disease states can be treated in accordance with this invention by administering an effective amount of a composition of the above formula wherein $A_b$ comprises a ligand capable of binding to an activated macrophage and wherein the group X comprises an immunogen, a cytotoxin, or a cytokine capable of altering macrophage function. Such macrophage targeting conjugates, when administered to a patient suffering from an activated macrophage mediated disease state, work to concentrate and associate the conjugated cytotoxin, immunogen, or cytokine with the population of activated macrophages to kill the activated macrophages or alter macrophage function. Elimination or deactivation of the activated macrophage population works to stop or reduce the activated macrophage mediated pathogenesis characteristic of the disease state being treated. The conjugate is typically administered parenterally as a composition comprising the conjugate and a pharmaceutically acceptable carrier therefor. Conjugate administration is typically continued until symptoms of the disease state are reduced or eliminated.

In one embodiment of the invention activated macrophage mediated disease states are monitored or diagnosed in a patient by administering a conjugate $A_b$-X wherein $A_b$ comprises a ligand capable of binding to activated macrophages and X comprises an imaging agent and thereafter scanning the patient with an imaging device capable of detecting localized concentration of the imaging agent. The imaging or diagnostic conjugates are, similar to those therapeutic conjugates outlined above, typically administered as a diagnostic composition comprising a conjugate and a pharmaceutically acceptable carrier. The composition is typically formulated for parenteral administration and is administered to the patient in an amount effective to enable imaging of the locale of activated macrophage populations. The nature of the imaging agent component of the conjugate is dictated by the imaging methodology. Thus, for example, the imaging agent can comprise a chelating moiety and a metal cation, for example, a radionuclide or a nuclear resonance imaging contrast agent, such as gadolinium. Typically the activated macrophage targeted imaging agent is administered to a patient, and following a period of time to allow delivery and concentration of the imaging agent in the activated macrophage cell populations, the patient is subjected to the imaging procedure and imaging is enabled by the targeted imaging agent.

The method of the present invention can be used for both human clinical medicine and veterinary applications. Thus, the host animals afflicted with the activated macrophage mediated disease state can be humans, or in the case of veterinary applications, they can be laboratory, agricultural, domestic or wild animals. The conjugates administered in accordance with the methods of this invention are preferably administered parenterally to the animal or patient suffering from the disease state, for example, intradermally, subcutaneously, intramuscularly, intraperitoneally, or intravenously. Alternatively, the conjugates can be administered to the animal or patient by other medically useful procedures and effective doses can be administered in standard or prolonged release dosage forms, such as a slow pump. The therapeutic method of the present invention may be used alone or in combination with other therapeutic methods recognized for the treatment of macrophage mediated disease states.

In the ligand conjugates of the general formula $A_b$-X in accordance with the present invention, the group $A_b$ is a ligand capable of binding to activated macrophages. Any of a wide number of macrophage binding moieties can be employed. Acceptable ligands include particularly folate receptor binding ligands and antibodies or antibody fragments capable of recognizing and specifically binding to surface moieties uniquely or preferentially expressed or presented in/on activated macrophages. In one embodiment the activated macrophage binding ligand is folic acid, a folic acid analog or other folate receptor binding molecules. Activated macrophages express a 38 LD GPI-anchored folate receptor that binds folate and folate-derivatized compounds with subnanomolar affinity (i.e., <1 nM). In another embodiment the activated macrophage binding ligand is a specific monoclonal or polyclonal antibody or Fab or scFv (i.e., a single chain variable region) fragments of antibodies capable of specific binding to activated macrophages.

The activated macrophage targeted conjugates used for diagnosing and monitoring disease states mediated by activated macrophages in accordance with this invention are formed to target and, thus, to concentrate an imaging agent at the site of activated macrophage populations in the diseased patient. In such conjugates of the formula $A_b$-X, $A_b$ is a ligand capable of binding to activated macrophages and the group X comprises an imaging agent. In one embodiment the imaging agent comprises a chelating agent and a metal cation, typically either a radionuclide or a nuclear magnetic resonance imaging enhancer or contrast agent, such as gadolinium. Such conjugates wherein the group $A_b$ is folic acid, a folic acid analog, or another folic acid receptor binding ligand are described in detail in U.S. Pat. No. 5,688,488, the specification of which is incorporated herein by reference. That patent, as well as related U.S. Pat. Nos. 5,416,016 and 5,108,921, each incorporated herein by reference, describe methods and examples for preparing chelate conjugates useful in accordance with the present invention. The present macrophage targeted imaging agents can be prepared and used following general protocols described in those earlier patents. The present diagnostic method, however, is based in part on the discovery that folate targeted conjugates can be used to concentrate conjugated imaging entities in and at activated macrophage populations enabling monitoring and diagnosis of disease states characterized by concentration of activated macrophages at the site of disease.

In accordance with one embodiment of the present invention there is provided a method of treating disease states mediated by activated macrophages by administering to a patient suffering from such disease state an effective amount of a composition comprising a conjugate of the general formula $A_b$-X wherein $A_b$ is as defined above and the group X comprises a cytotoxin, an immunogen, or a compound capable of altering macrophage function. Exemplary of cytotoxic moieties useful for forming conjugates for use in accordance with the present method include clodronate, anthrax, Pseudomonas exotoxin, typically modified so that these cytotoxic moieties do not bind to normal cells, and other toxins or cytotoxic agents including art-recognized chemotherapeutic agents such as adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, and bleomycin, nitrogen mustards, nitrosureas, vincristine, vinblastine, inflammatory and proinflammatory agents, and the like. Such toxins or cytotoxic components can be directly conjugated to the activated macrophage binding moiety, for example, folate or other folate receptor binding ligands, or they can be formulated in liposomes which themselves are targeted as conjugates of macrophage binding entities typically by covalent linkages to component phospholipids. Similarly, when the group X comprises a compound capable of altering a macrophage function, for example, a cytokine such as IL-10 or IL-11, the cytokine can be covalently linked to the targeting moiety $A_b$, for example, a folate receptor binding ligand or an antibody or antibody fragment directly, or the macrophage function altering cytokine can be encapsulated in a liposome which is itself targeted to activated macrophages by pendent macrophage targeting entities $A_b$ covalently linked to one or more phospholipid liposome components.

In another embodiment the ligand-immunogen conjugates can be administered in combination with a cytotoxic compound. The compounds listed in the preceding paragraph are among the compounds suitable for this purpose.

In another method of treatment embodiment of the present invention the group X in the activated macrophage targeted conjugate $A_b$-X, comprises an immunogen, the ligand-immunogen conjugates being effective to "label" the population of activated macrophages responsible for disease pathogenesis in the patient suffering from the disease for specific elimination by an endogenous immune response or by co-administered antibodies. The use of ligand-immunogen conjugates in the method of treatment in accordance with this invention works to enhance an immune response-mediated elimination of the activated macrophage population. Such can be effected through an endogenous immune response or by a passive immune response effected by co-administered antibodies. The endogenous immune response may include a humoral response, a cell-mediated immune response, and any other immune response endogenous to the host animal, including complement-mediated cell lysis, antibody-dependent cell-mediated cytotoxicity (ADCC), antibody opsonization leading to phagocytosis, clustering of receptors upon antibody binding resulting in signaling of apoptosis, antiproliferation, or differentiation, and direct immune cell recognition of the delivered antigen/hapten. It is also contemplated that the endogenous immune response will employ the secretion of cytokines that regulate such processes as the multiplication and migration of immune cells. The endogenous immune response may include the participation of such immune cell types as B cells, T cells, including helper and cytotoxic T cells, macrophages, natural killer cells, neutrophils, LAK cells, and the like.

In another embodiment, the ligand-immunogen conjugate can be internalized and the immunogen can be degraded and presented on the macrophage cell surface for recognition by immune cells to elicit an immune response directed against macrophages presenting the degraded immunogen.

The humoral response may be a response induced by such processes as normally scheduled vaccination, or active immunization with a natural antigen or an unnatural antigen or hapten, e.g., fluorescein isothiocyanate (FITC), with the unnatural antigen inducing a novel immunity. Active immunization involves multiple injections of the unnatural antigen or hapten scheduled outside of a normal vaccination regimen to induce the novel immunity. The humoral response may also result from an innate immunity where the host animal has a natural preexisting immunity, such as an immunity to α-galactosyl groups. Alternatively, a passive immunity may be established by administering antibodies to the host animal such as natural antibodies collected from serum or monoclonal antibodies that may or may not be genetically engineered antibodies, including humanized antibodies. The utilization of a particular amount of an antibody reagent to develop a passive immunity, and the use of a ligand-immunogen conjugate wherein the passively administered antibodies are directed to the immunogen, would provide the advantage of a standard set of reagents to be used in cases where a patient's preexisting antibody titer to other potential antigens is not therapeutically useful. The passively administered antibodies may be "co-administered" with the ligand-immunogen conjugate, and co-administration is defined as administration of antibodies at a time prior to, at the same time as, or at a time following administration of the ligand-immunogen conjugate. It is contemplated that the preexisting antibodies, induced antibodies, or passively administered antibodies will be redirected to the activated macrophages by preferential binding of the ligand-immunogen conjugates to the activated macrophage cell populations, and such pathogenic cells are killed by complement-mediated lysis, ADCC, antibody-dependent phagocytosis, or antibody clustering of receptors. The cytotoxic process may also involve other types of immune responses, such as cell-mediated immunity, as well as secondary responses that arise when the attracted antigen-presenting cells phagocytose the activated macrophages and present antigens of such cells to the immune system for elimination of other activated macrophages presenting such antigens.

Acceptable immunogens for use in preparing the conjugates used in the method of treatment of the present invention are immunogens that are capable of eliciting antibody production in a host animal or that have previously elicited antibody production in a host animal, resulting in a preexisting immunity, or that constitute part of the innate immune system. Alternatively, antibodies directed against the immunogen may be administered to the host animal to establish a passive immunity. Suitable immunogens for use in the invention include antigens or antigenic peptides against which a preexisting immunity has developed via normally scheduled vaccinations or prior natural exposure to such agents such as polio virus, tetanus, typhus, rubella, measles, mumps, pertussis, tuberculosis and influenza antigens and α-galactosyl groups. In such cases, the ligand-immunogen conjugates will be used to redirect a previously acquired humoral or cellular immunity to a population of activated macrophages in the host animal for elimination of such cells. Other suitable immunogens include antigens or antigenic peptides to which the host animal has developed a novel immunity through immunization against an unnatural antigen or hapten, for example, fluorescein isothiocyanate (FITC) or dinitrophenyl and antigens against which an innate immunity exists, for example, super antigens and muramyl dipeptide. It is also contemplated that MHC I restricted peptides could be linked to the ligand for use in redirecting cellular immunity to macrophages and eliciting T cell killing of macrophages.

The macrophage binding ligands and immunogens, cytotoxic agents, cytokines or imaging agents, as the case may be in forming conjugates for use in accordance with the present invention, may be conjugated by using any art-recognized method for forming a complex. This can include covalent, ionic, or hydrogen bonding of the ligand to the immunogen, either directly or indirectly via a linking group such as a divalent linker. The conjugate is typically formed by covalent bonding of the ligand to the targeted entity through the formation of amide, ester or imino bonds between acid, aldehyde, hydroxy, amino, or hydrazo groups on the respective components of the complex. Alternatively, as mentioned above, the ligand complex can be one comprising a liposome wherein the targeted entity (that is, the imaging agent, or the immunogen, cytotoxic agent or macrophage function altering agent) is contained within a liposome which is itself covalently linked to the activated macrophage binding ligand.

In one embodiment of the invention the ligand is folic acid, an analog of folic acid, or any other folate receptor binding molecule, and the folate ligand is conjugated to the targeted entity by a procedure that utilizes trifluoroacetic anhydride to prepare γ-esters of folic acid via a pteroyl azide intermediate. This procedure results in the synthesis of a folate ligand, conjugated to the targeted entity only through the γ-carboxy group of the glutamic acid groups of folate. Alternatively, folic acid analogs can be coupled through the α-carboxy moiety of the glutamic acid group or both the α and γ carboxylic acid entities.

The conjugates used in accordance with this invention of the formula $A_b$-X are used in one aspect of this invention to formulate therapeutic or diagnostic compositions comprising effective amounts of the conjugate and an acceptable carrier therefor. Typically such compositions are formulated for parenteral use. The amount of the conjugate effective for use in accordance with the invention depends on many parameters, including the nature of the disease being treated or diagnosed, the molecular weight of the conjugate, its route of administration and its tissue distribution, and the possibility of co-usage of other therapeutic or diagnostic agents. The effective amount to be administered to a patient is typically based on body surface area, patient weight and physician assessment of patient condition. An effective amount can range from about to 1 ng/kg to about 1 mg/kg, more typically from about 1 μg/kg to about 500 μg/kg, and most typically from about 1 μg/kg to about 100 μg/kg.

When used for monitoring or diagnosis, imaging procedures are typically carried out about 1 to about 6 hours post administration of the activated macrophage targeted imaging agent.

Any effective regimen for administering the ligand conjugates can be used. For example, the ligand conjugates can be administered as single doses, or they can be divided and administered as a multiple-dose daily regimen. Further, a staggered regimen, for example, one to three days per week can be used as an alternative to daily treatment, and for the purpose of defining this invention such an intermittent or staggered daily regimen is considered to be equivalent to every day treatment and within the scope of this invention. In one embodiment of the invention the patient is treated with multiple injections of the ligand conjugate wherein the targeted entity is an immunogen or a cytotoxic agent to eliminate the population of pathogenic activated macrophages. In one embodiment, the patient is treated, for example, injected multiple times with the ligand conjugate at, for example, at 12-72 hour intervals or at 48-72 hour intervals. Additional injections of the ligand conjugate can be administered to the patient at intervals of days or months after the initial injections, and the additional injections prevent recurrence of disease. Alternatively, the ligand conjugates may be administered prophylactically to prevent the occurrence of disease in patients known to be disposed to development of activated macrophage mediated disease states. In one embodiment of the invention more than one type of ligand conjugate can be used, for example, the host animal may be pre-immunized with fluorescein isothiocyanate and dinitrophenyl and subsequently treated with fluorescein isothiocyanate and dinitrophenyl linked to the same or different activated macrophage targeting ligands in a co-dosing protocol.

The ligand conjugates are administered in accordance with this invention parenterally and most typically by intraperitoneal injections, subcutaneous injections, intramuscular injections, intravenous injections or intrathecal injections. The ligand conjugates can also be delivered to a patient using an osmotic pump. Examples of parenteral dosage forms include aqueous solutions of the conjugate, for example, solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate. In another aspect of the invention, the ligand conjugates can be formulated as one of any of a number of prolonged release dosage forms known in the art such as, for example, the biodegradable carbohydrate matrices described in U.S. Pat. Nos. 4,713,249; 5,266,333; and 5,417,982, the disclosures of which are incorporated herein by reference.

EXAMPLE 1

Materials

EC20 (a folate-linked chelator $^{99m}$Tc), EC28 (the same $^{99m}$Tc chelate complex without folate), and folate-fluorescein isothiocyanate (folate-FITC) were gifts from Endocyte, Inc. (West Lafayette, Ind.). Heat-killed *Mycoplasma butericum* was purchased from BD Biosciences (Sparks, Md.). Folic acid, light mineral oil, clodronate, collagenase-A, and streptavidin-R-phycoerythrin were obtained from Sigma Chemical Co. (St. Louis, Mo.), and Dubelco's Modified Eagle Medium (DMEM) was from Gibco-BRL (Gathersberg, Md.). $^3$H-folic acid was obtained from American Radiolabeled Chemicals, Inc. (St. Louis, Mo.) and Microcon®-30 membranes were purchased from Millipore Corp. (Bedford, Mass.). RK-4-biotin and ED2-R-phycoerythrin antibodies were acquired from Bachem Biosciences, Inc. (Philadelphia, Pa.) and Accurate Chemical and Scientific Corp. (Westbury, N.Y.), respectively.

EXAMPLE 2

Animal Model of Arthritis

Arthritis was induced in 150-200 g female Lewis rats (Charles River Laboratories, Inc., Wilmington, Mass.), n=4/ dose group. Briefly, 0.5 mg of heat-killed *Mycoplasma*

*butericum*, suspended in mineral oil (5 mg/ml), was injected on day 0 into the left hind foot of rats following anesthesia with ketamine and xylazine. Disease was allowed to progress for 21 days, and animals were weighed on a daily basis to ensure the status of their health. All treated animals developed arthritis, as evidenced by dramatic swelling in the injected paw, progressive swelling in all noninjected limbs due to the systemic progression of arthritis, and radiographic analysis of affected limbs. All rats were maintained on a folate-deficient diet (DYETS, Inc., Bethlehem, Pa.) for 3 weeks prior to administration of folate-FITC in order to lower serum folate levels to physiologically relevant concentrations. Control rats were also maintained on a folate-deficient diet but not induced to develop arthritis.

EXAMPLE 3

Elimination of Endogenous Macrophages

Evaluation of macrophage independent uptake of the folate-linked imaging agent was accomplished by killing endogenous macrophages with liposomal clodronate. Liposomes were formed by rehydrating a thin film of egg phosphatidylcholine (60 mole %) and cholesterol (40 mole %) in an isotonic clodronate solution (250 mg/ml). Small unilamellar vesicles were then generated by extrusion of the liposomes ten times through a 100 nm polycarbonate membrane using a 10 ml thermobarrel extruder (Lipex Biomembranes, Vancouver, Canada). Unencapsulated clodronate was removed by dialysis through a Spectrapor 300,000 $M_r$-cutoff cellulose acetate membrane (Spectrum Laboratories, Rancho Domingues, Calif.), and the clodronate concentration in the retained liposomes was determined as described in *J. Microencapsul.* 3(2) 109-14 (1986). Seventeen days following induction of the arthritis and three days prior to administration of the imaging agent (EC20), rats destined for macrophage depletion received a single intraperitoneal injection of clodronate liposomes containing 20 mg clodronate.

EXAMPLE 4

Scintigraphy and Biodistribution Analysis

Twelve hours prior to administration of imaging agent, all animals received 5 ml of normal saline subcutaneously to ensure proper excretion of unbound imaging agent. Twenty-one days following induction of arthritis, rats (n=3 per group) were injected intraperitoneally with 500 µCi (2.3 nmoles/rat) of either EC20 (folate+chelator), EC20+500-fold molar excess folic acid, or EC28 (no folate moiety). Four hours later, rats underwent either nuclear scintigraphic imaging or biodistribution analysis.

For scintigraphy, rats were anesthetized with ketamine and xylazine, and positioned in ventral recumbency on the image acquisition surface. Image acquisition was performed for one minute at a count rate of 50-75,000 counts per minute using a Technicare Omega 500 Sigma 410 Radioisotope Gamma Camera. Following acquisition of whole body images, radiation of the upper body (above the stifles) was blocked using ⅛" lead plates, and images of the posterior limbs were obtained. All data were analyzed using a Medasys™ MS-DOS-based computer equipped with Medasys™ Pinnacle software.

For biodistribution analysis, rats were euthanized by intraperitoneal injection of nebutal or pentobarbitol sodium. Liver, spleen, heart, lungs, intestine, and kidneys were then harvested and radiation in each tissue was determined by counting in a gamma counter (Packard BioScience Co., Meridian, Conn.).

EXAMPLE 5

Assay of Tissue Folate Receptor Levels

Folate receptor levels in each tissue were determined follows. Briefly, tissues were homogenized and cell membranes were isolated by centrifugation.

Membrane proteins were solubilized overnight, transferred into a Microcon®-30 filtration device, and incubated with 50 nM $^3$H-folic acid. A duplicate of each sample, used to determine non-specific binding, was also exposed to 50 nM $^3$H-folic acid, but in the presence of 1000-fold excess unlabeled folic acid. After unbound $^3$H-folic acid was washed through the membrane, membrane protein with bound $^3$H-folic acid was recovered and counted in a scintillation counter (Packard BioScience Co.) to determine the number of active folate receptors per gram of tissue.

EXAMPLE 6

Identification of the Folate Receptor Expressing Cell Type in Liver

Arthritic and healthy rats were first anesthetized with ketamine and xylazine, and then a midline incision was made, starting in the lower abdomen and extending through the thoracic cavity. A 24-gauge catheter was inserted into the hepatic vein, and a 24-gauge needle was inserted in the cardiac left ventricle to serve as an outlet for the perfusion fluid. Rats were then perfused by delivery of normal saline, followed by collagenase A solution (0.05% in Gey's balanced salt solution) through the catheter. Each solution was perfused for two minutes at a rate of 20 ml/minute. Immediately after perfusion, livers were removed and the membranous outer tissue was dissected away. The remaining gelatinous tissue was suspended in collagenase-A solution (0.025% in DMEM) and incubated at 37° C. for two hours in the presence of 1 µM folate-FITC or 1 µM folate-FITC+1 mM folic acid. Cells were then washed three times to removed unbound folate-FITC and immediately prepared for flow cytometry.

EXAMPLE 7

Flow Cytometry Sample Preparation and Analysis

Liver cell preparations, which had been exposed to folate-FITC, were treated for 10 mm at 4° C. with ammonium chloride lysis buffer (150 mM $NH_4Cl$, 10 mM $KHCO_3$, 1 mM EDTA, pH 7.4) to lyse red blood cells. Following three washes with phosphate buffered saline, the remaining cells were incubated for 1 h at 4° C. with either ED2 R-Phycoerythrin-labeled mouse anti-rat macrophage antibody, or RK-4 biotin-labeled mouse-anti rat granulocyte antibody. Cells were again washed two times, and those that had received the biotinylated primary antibody were further incubated with streptavidin-R-Phycoerythrin for 30 minutes. Following two final washes, cells were examined for FITC and phycoerythrin dual color staining on a FACScan Coulter XL flow cytometer.

EXAMPLE 8

Immunotherapy Mediated Protection Against Adjuvant-Induced Arthritis

Figure 9:
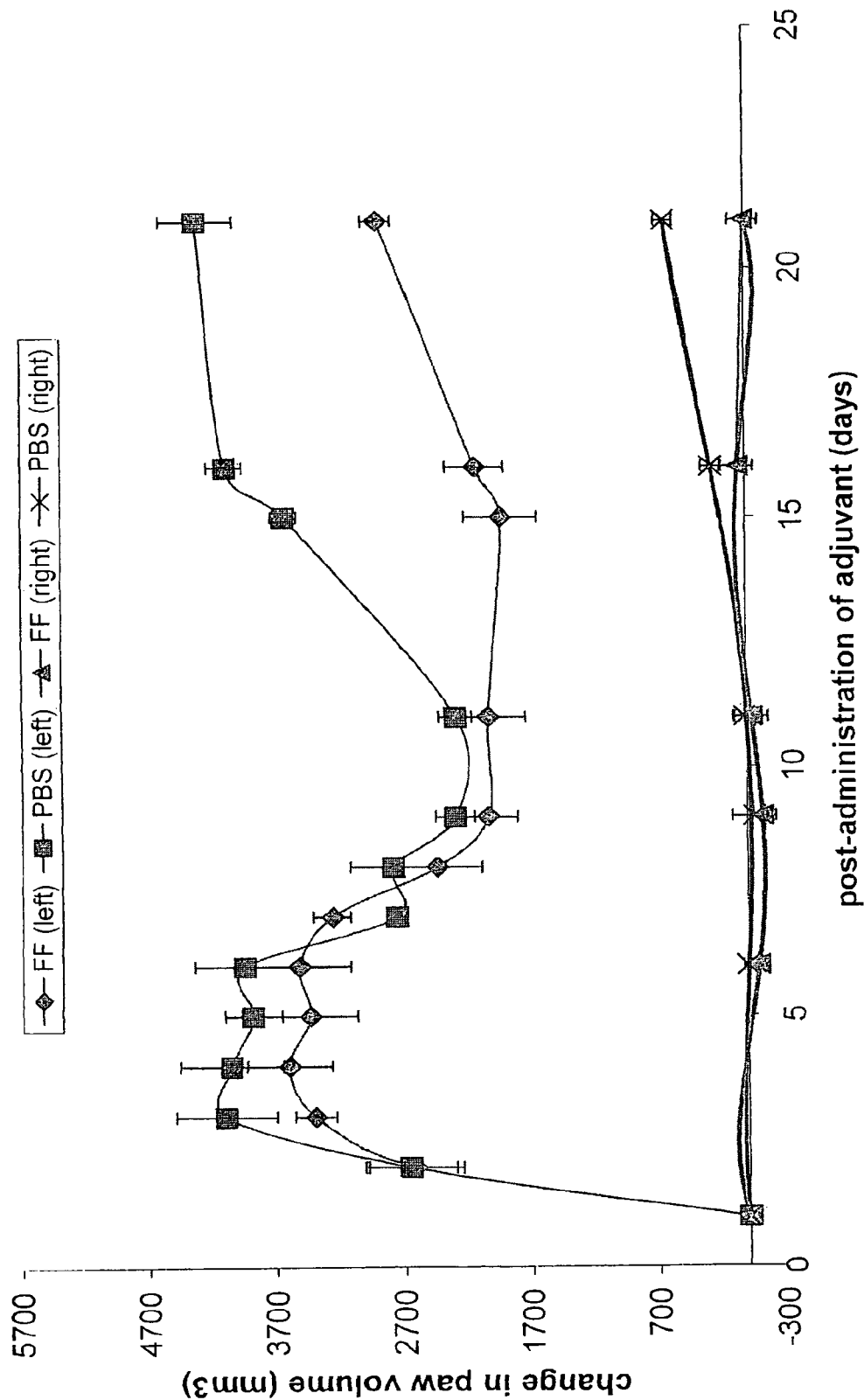
FIG. 9 demonstrates immunotherapy mediated protection against adjuvant-induced arthritis (diamonds represent folate-FITC (left foot), squares represent PBS (left foot), triangles represent folate-FITC (right foot), and x's represent PBS (right foot)).

The protocol described in Example 2 for arthritis induction was followed. The efficacy of a folate-FITC conjugate (folate-fluorescein isothiocyanate conjugate) against adjuvant-induced arthritis in rats was investigated. Each rat used in the experiment was immunized at the base of the tail with FITC-KLH (150 μg) to induce antibodies against FITC on days −38 and −10 before administration of *Mycoplasma butericum* (adjuvant) to induce arthritis. The immunization of FITC-KLH was done in combination with an adjuvant (i.e., such as TiterMax Gold (150 μg), Alum (150 μg), or GPI-100 (150 μg) which are all adjuvants to induce antibodies against FITC as opposed to the adjuvant used to induce arthritis). The immunized animals were then injected on day 0 in the left foot pad with 0.5 mg of heat-killed *Mycoplasma butyricum* (adjuvant) to initiate development of arthritis. Then on days 1, 2, 3, 9, 11, and 14, post-adjuvant (*Mycoplasma butyricum*) injection, the rats were injected intraperitoneally with either saline (control rats) or 2000 nmoles/kg of folate-FITC (FF). Calipers were used to measure left and right foot dimensions daily. With reference to FIG. 9, those measurements were plotted for both the adjuvant-injected feet (top two curves) and the non-treated feet (bottom two curves). A sudden increase in swelling of the adjuvant-injected feet is due to influx of neutrophils which have no folate receptors. Consequently, the immunotherapy has no impact on this phase of paw swelling. However, after about 10 days, activated macrophages invade both injected feet and uninjected feet, causing bone degradation and further inflammation. These activated macrophages have functional folate receptors, and, as shown, they are eliminated or reduced by binding folate-hapten conjugates such as folate-FITC.

EXAMPLE 9

Folate-Targeted Imaging of Arthritic Rats

Figure 8:
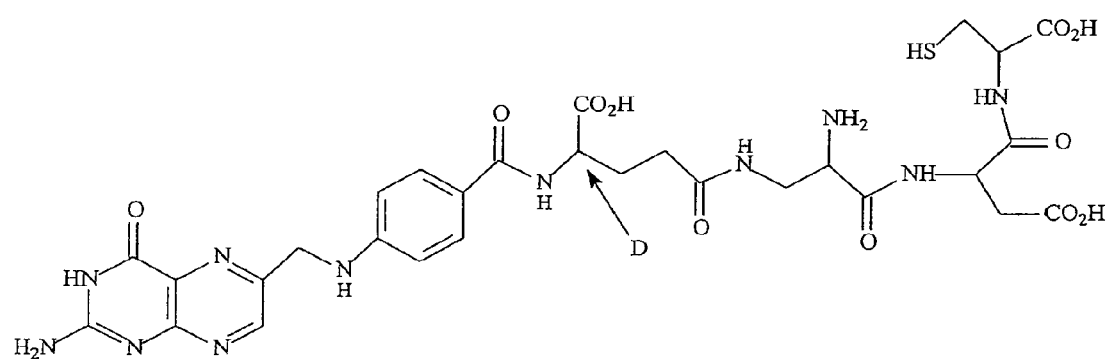
FIG. 8 shows a chemical structure representing the folate-linked chelator EC20.

The protocols described in Examples 2 and 4 were followed. As noted above, activated but not resting macrophages express a receptor for the vitamin folic acid. To determine whether folate might be exploited to target $^{99m}$Tc to sites of arthritic inflammation, EC20, a folate-linked chelator of $^{99m}$Tc (see FIG. 8) was administered intraperitoneally to rats (n=5/group) and scintigraphic images were acquired with a gamma camera. Due to the rapid clearance of EC20, excellent contrast was obtained by at least four hours post-administration (FIG. 1). Importantly, whole body uptake was significantly more intense in arthritic rats compared to healthy rats, and this uptake was greatly reduced when EC20 was administered together with a saturating dose of free folic acid. This suggests that uptake by all tissues is primarily determined by a folic-specific receptor.

Intense organ uptake of EC20 prevented visualization of limbs in whole body images of the arthritic rats. However, images of posterior limbs could be easily acquired when mid and upper body radiation was shielded. With such shielding, arthritic limbs displayed much greater EC20 uptake than healthy extremities, and this uptake was completely eliminated in the presence of excess free folic acid (FIG. 1). Furthermore, the left rear foot of the arthritic animals, where inflammation was most severe, displayed greater uptake than the less severely affected right rear foot (FIG. 1).

Figure 2:
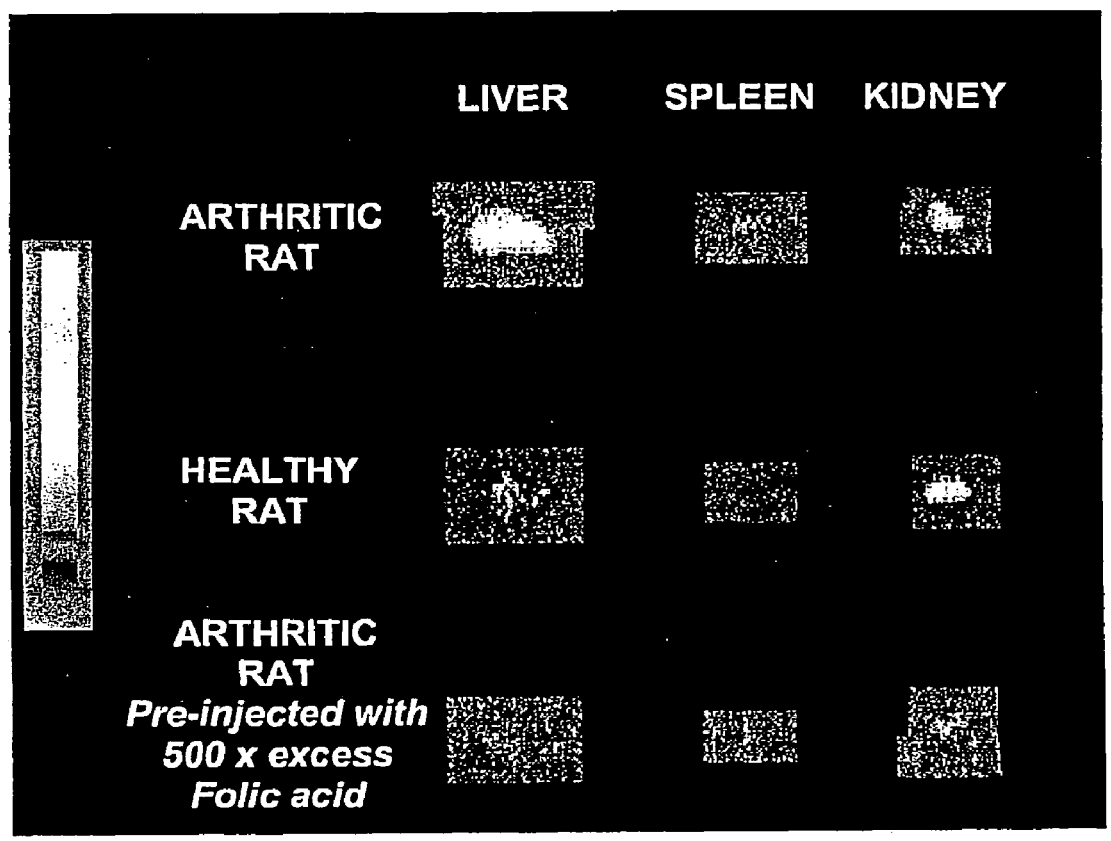
FIG. 2 shows folate-targeted imaging of arthritic rats (assessment of liver, spleen and kidney by scintigraphy).

From the whole body images, it could be concluded that abdominal organs were responsible for a majority of EC20 uptake in the arthritic animals. To confirm this assessment, liver, spleen and kidney were removed and imaged separately (FIG. 2). Livers of arthritic rats demonstrated the highest uptake of EC20, while livers of healthy rats displayed minimal uptake. Only those spleens taken from arthritic rats could be visualized. Free folic acid completely blocked EC20 uptake in liver and spleen, however, the free vitamin only partially decreased uptake by the kidney.

EXAMPLE 10

Effects of Macrophage Depletion

Figure 3:
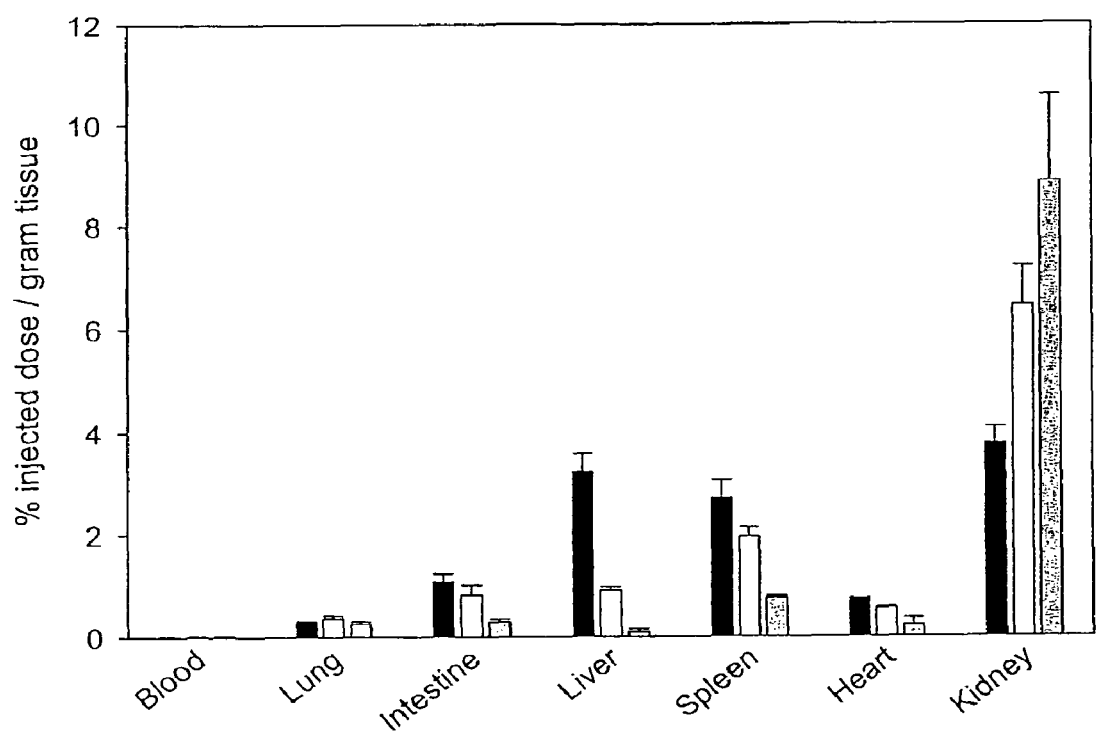
FIG. 3 shows effects of macrophage depletion (black bars represent arthritic rats, light gray bars represent healthy rats, and dark gray bars represent arthritic rats depleted of macrophages by clodronate treatment).

The protocols described in Examples 2, 3, and 4 were followed, except that 0.25 mCi of EC20 was administered. In order to determine whether macrophages might be responsible for the uptake of EC20, resident macrophages were systemically eliminated from arthritic rats using a liposomal clodronate preparation (n=3 rats/group). By four days after clodronate treatment, evaluation of paw size revealed that clodronate-treated rats were significantly less inflamed than untreated rats (data not shown). To determine whether macrophage elimination would influence uptake of the folate-linked imaging agent, EC20 biodistribution analysis was then performed on the clodronate-treated rats and compared to the same analysis of both healthy rats and arthritic rats not treated with clodronate. As shown in FIG. 3 (black bars represent arthritic rats, light gray bars represent healthy rats, and dark gray bars represent arthritic rats depleted of macrophages by clodronate treatment), depletion of macrophages decreased liver uptake of EC20~20-fold in arthritic rats, while retention in the spleen and intestine was reduced by a factor of three. In most tissues, clodronate treatment depressed EC20 uptake even below those levels observed in healthy rats, confirming the hypothesis that activated macrophages account for most of EC20 retention in normal tissues. In contrast, kidney uptake of EC20 was elevated in rats depleted of macrophages, most likely because the decreased internalization of EC20 by activated macrophages rendered more EC20 available for binding to kidney folate receptors.

EXAMPLE 11

Folate Receptor-Mediated Uptake of EC20 in Arthritic Tissues

Figure 4:
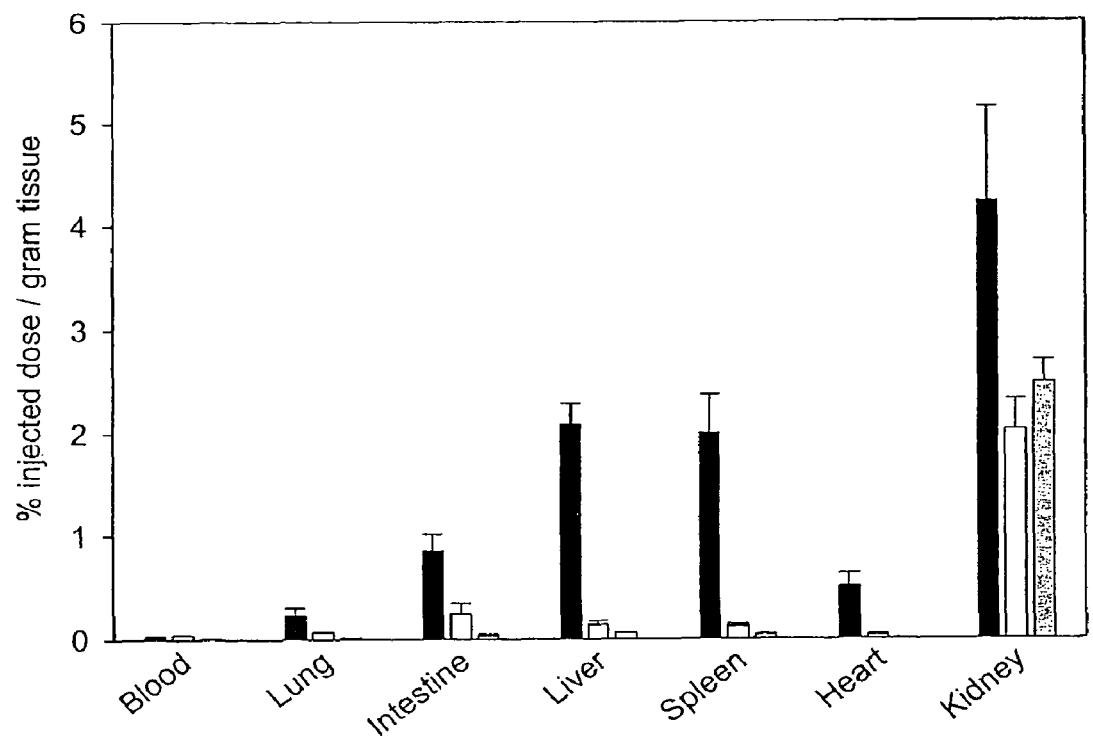
FIG. 4 shows folate receptor-mediated uptake of EC20 in arthritic tissues (light gray bars represent biodistribution of EC20 in the presence of a 500-fold excess of free folic acid, black bars represent biodistribution of EC20 in the absence of a 500-fold excess of free folic acid, dark gray bars represent the biodistribution of the same complex lacking a folate moiety (EC28)).

The protocols described in Examples 2 and 4 were followed. Two additional biodistribution studies were conducted to confirm that EC20 uptake by tissues of arthritic rats is mediated by the folate receptor (n=3 rats/group). First, the biodistribution of EC20 was examined in the presence (light gray bars) and absence (black bars) of a 500-fold excess of free folic acid. As seen in FIG. 4, almost complete elimination of EC20 uptake was observed in all tissues except kidney, indicating that binding was indeed mediated by a folate receptor. In fact, excess folic acid competitively reduced EC20 retention in liver, spleen, heart, lung, intestine and blood to near background levels (FIG. 4). Second, to confirm the role of folate in EC20-mediated targeting of the chelated $^{99m}$Tc, the biodistribution of the same complex lacking a folate moiety (EC28) was also examined (dark gray bars). As also displayed in FIG. 4, uptake of EC28 was negligible in all tissues except kidney, where retention of the non-targeted complex was similar to that of EC20 in the presence of competing folic acid.

EXAMPLE 12

Folate Receptor Expression in Various Tissues of Arthritic Rats

Figure 5:
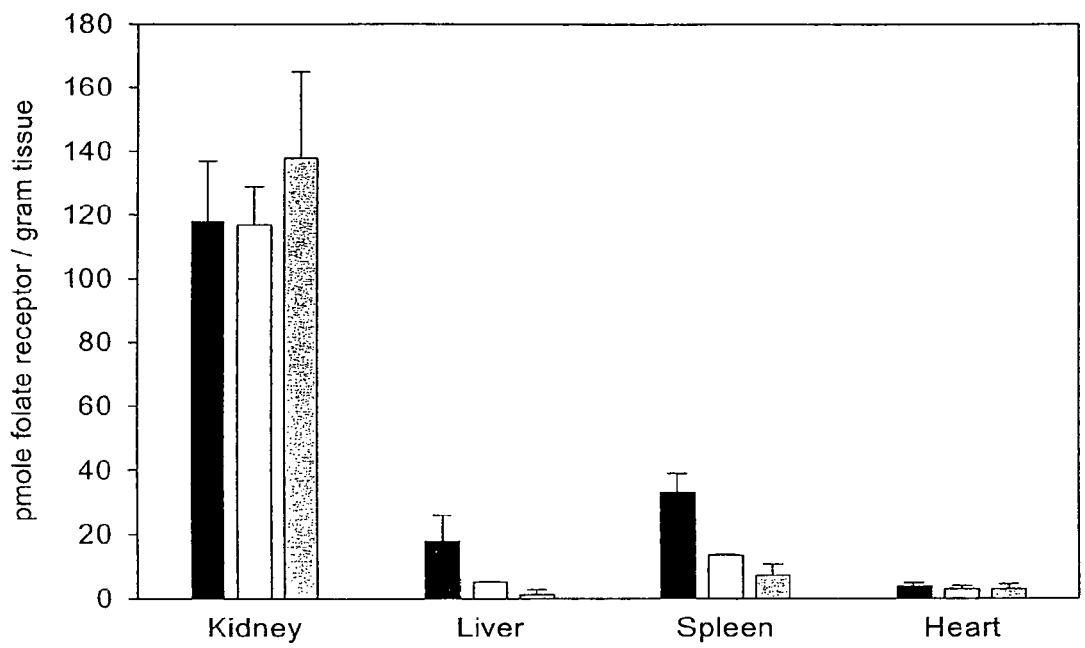
FIG. 5 shows folate receptor expression in various tissues of arthritic rats (black bars represent arthritic rats, light gray bars represent healthy rats, and dark gray bars represent arthritic rats depleted of macrophages by clodronate treatment).

The protocols described in Examples 2, 4, and 5 were used. The above results suggest that the folate receptor is responsible for tissue uptake of EC20. In order to confirm this, Applicants attempted to directly quantitate the folate binding protein in various rat tissues. Active folate receptor could be detected in each of the major organs examined, and FR levels were significantly increased in arthritic rats (FIG. 5; black bars=arthritic rats; light gray bars=healthy rats). Further, FR content correlated well with uptake of EC20 seen in the biodistribution studies. In fact, the FR assay revealed roughly equivalent levels of receptor in arthritic liver and spleen, in accordance with the similar uptake of EC20 by the same organs (FIG. 4). Significantly, systemic elimination of macrophages by clodronate treatment (dark gray bars) lowered folate receptor levels in all arthritic tissues (FIG. 5), also in good agreement with the EC20 biodistribution analysis. Finally, the FR assay confirmed that neither induction of arthritis nor clodronate treatment alters the levels of FR in kidney or heart, where FR is not thought to be associated with activated macrophages.

EXAMPLE 13

Figure 6:
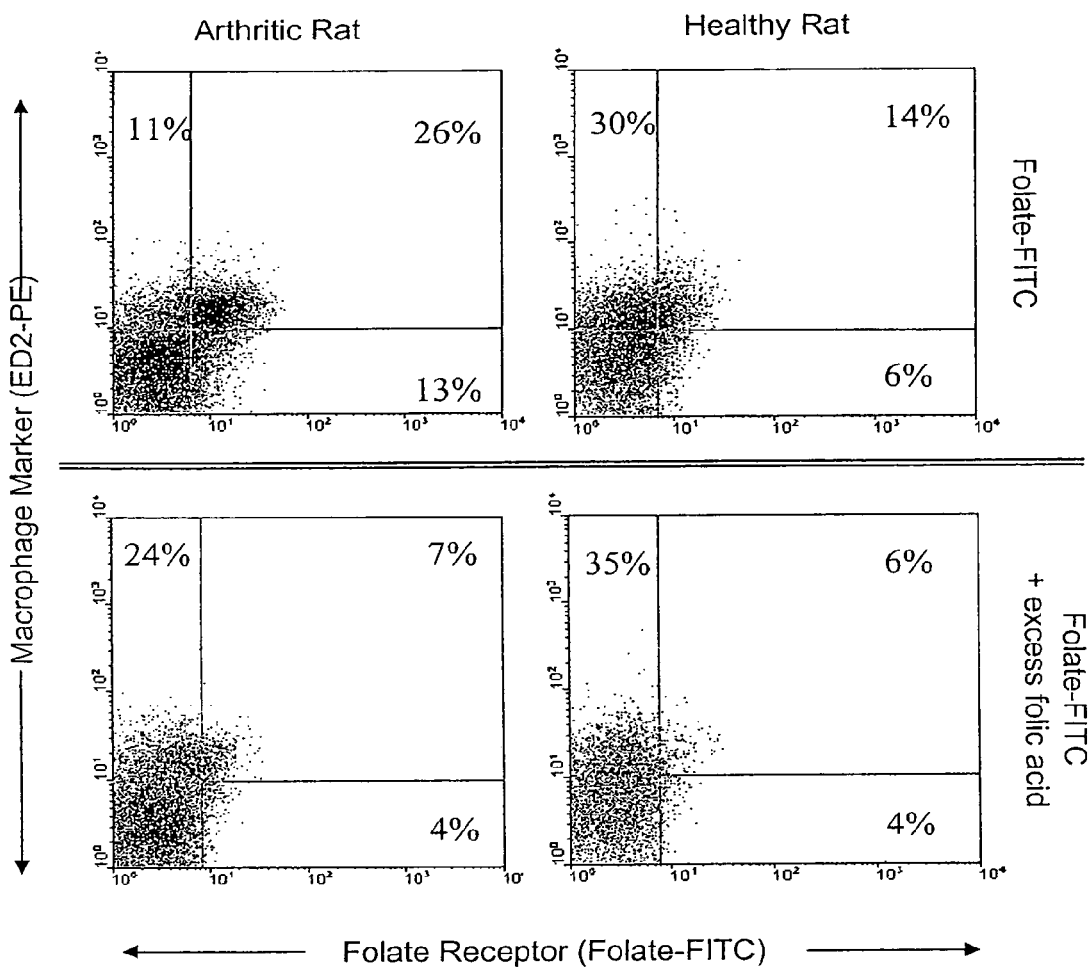
FIG. 6 shows expression of a functional folate receptor on liver macrophages of arthritic rats.

Expression of a Functional Folate Receptor on Liver Macrophages of Arthritic Rats The protocols described in Examples 2, 4, 6 and 7 were used. To further confirm that the elevated uptake of EC20 in livers of arthritic rats is due to a macrophage population, livers were resected from collagenase-perfused rats and their disaggregated cells examined for folate conjugate uptake, using folate-FITC as a fluorescent marker for FR expression. By also labeling the same liver cell suspension with an antibody specific for rat liver macrophages, it was possible to demonstrate that macrophages are indeed the cell type that expresses elevated levels of folate receptor in arthritic animals (FIG. 6). Thus, flow cytometric analysis revealed that 70% of the liver macrophages of arthritic rats bound folate-FITC compared to only 30% of the liver macrophages of healthy rats (FIG. 6). Further, the FITC intensity of the arthritic macrophages was higher than that of macrophages from healthy livers. Since binding of folate-FITC was suppressed in the presence of an excess of free folic acid (1 mM), we concluded that uptake of the folate conjugate by liver macrophages was mediated by the folate receptor.

Using an antibody specific for granulocytes, we also examined whether tissue infiltrating neutrophils might take up folate conjugates. Although very few neutrophils were found in the liver, those that were detected exhibited no binding capacity for folate-FITC (data not shown). Mac-1+peripheral blood cells were also tested and similarly found to have no binding affinity for the folate-conjugate (data not shown). In fact, no peripheral blood cells sorted positive for FITC fluorescence, suggesting that only resident tissue macrophages (and clearly only a subpopulation of those) express FR in the liver.

Figure 7:
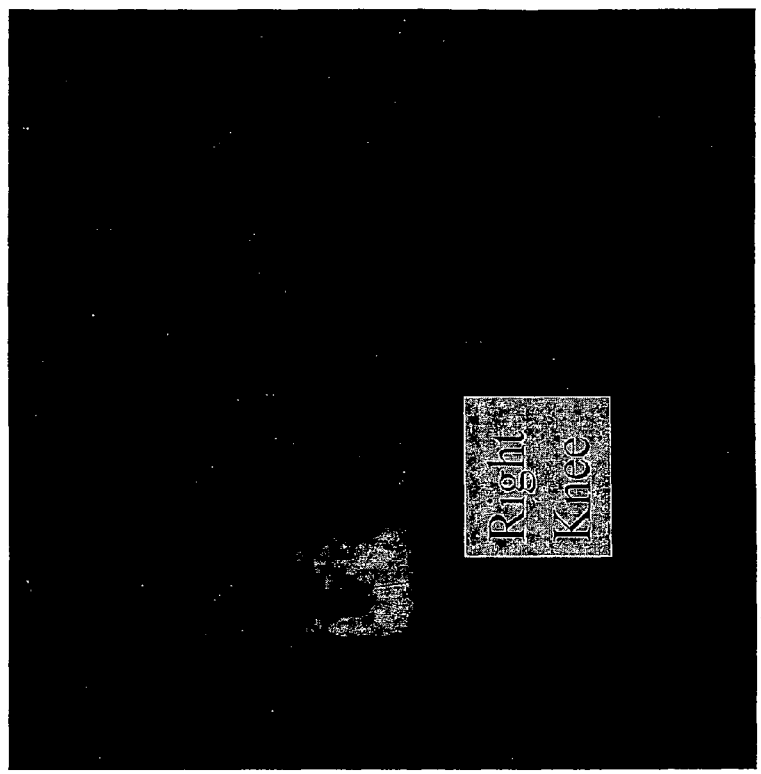
FIG. 7 shows increased uptake of a folate-targeted imaging agent in a patient with an inflamed joint.

Finally, to begin to explore whether activated macrophages might be targeted with folate-linked drugs in human patients, we obtained permission to examine the whole body images of the 28 suspected ovarian cancer patients enrolled in a recently completed clinical trial of the gamma imaging agent, $^{111}$In-DTPA-Folate. As shown in FIG. 7, one patient displayed significant imaging agent uptake in the right knee, but not the left knee. Importantly, no other patients demonstrated any measurable joint uptake. Upon request, the attending physician contacted the anonymous patient and inquired whether she had been experiencing any chronic joint discomfort. The physician responded that the patient reported arthritis in the right knee.

Discussion

Activated macrophages are thought to be intimately involved in the pathogenesis of rheumatoid arthritis. Activated macrophages directly destroy joint tissue by secreting metalloproteinases and attracting/activating other immune cells by releasing cytokines. The quantitation of activated macrophages in joint tissues might be of diagnostic value, since activated macrophage content correlates well with articular destruction and poor disease prognosis in humans.

Gamma camera scintigraphy of rats receiving EC20 demonstrated that arthritic appendages are indeed illuminated by folate-targeted $^{99m}$Tc. In contrast, the legs and feet of healthy rats could not be visualized, demonstrating the selectivity of the imaging agent for arthritis applications. Although the intensities of internal organs also increased in adjuvant-induced arthritis, interference from such tissues did not appear to compromise the methodology, since gamma radiation from internal, organs could be easily screened. The fact that excellent contrast can be obtained within one to two hours of EC20 injection further shows that imaging agent administration, gamma camera scintigraphy, and image analysis can be completed during the same examination.

Systemic activation of macrophages has been documented in rats with adjuvant-induced arthritis. Thus, it was important to establish the specific participation of macrophages in the elevated uptake of EC20, since a folate-targeted imaging agent had never previously been examined in arthritic animals. Three experiments were conducted for this purpose. First, clodronate-loaded liposomes were employed to systemically deplete macrophages from the treated rats. Not only were the resulting tissue FR levels greatly reduced, but uptake of EC20 in the macrophage-rich organs was also nearly eliminated, suggesting that resident macrophages can indeed account for both FR expression and EC20 retention in the RES organs. Second, liver cells were disaggregated by collagenase treatment and individual cells were evaluated for folate conjugate uptake. As noted in FIG. 6, the vast majority of cells testing positive for folate conjugate uptake also sorted positive for the macrophage marker, ED2, confirming that FR is indeed present on the macrophages. Finally, because other immune and myelocytic cells are known to be elevated in tissues of rats with adjuvant-induced arthritis, it was conceivable that still another extravasating blood cell type might be involved in the uptake of EC20. However, neither liver-infiltrating granulocytes nor any blood cell in circulation displayed any capacity to bind folate-FITC. Thus, activated macrophages would seem to be the predominant cell type internalizing folate conjugates in the organs of arthritic rats.

It was surprising to find that up to 30% of the liver macrophages in healthy rats also expressed the folate receptor (FIG. 6). Since a functional folate receptor is not found on resting synovial macrophages, it is tempting to speculate that the folate-FITC binding fraction in the healthy rats might also constitute an activated population. Two observations may support this conjecture. First, activated macrophages are also found in healthy tissues following exposure to immune stimulants such as foreign antigens. Given the role of the liver in clearing foreign substances from the body, a low level of resident macrophage activation does not seem unreasonable. Second, the folate-FITC (and EC20) binding population of liver cells increased significantly upon induction of localized inflammation and systemic macrophage activation.

With the ability to exploit folate to deliver attached molecules to activated macrophages now established, folate-linked imaging agents will allow the early development or continued progression of rheumatoid arthritis to be assessed.

Since graft versus host disease, multiple sclerosis, Crohn's disease, ulcerative colitis, psoriasis, osteomyelitis, and even atherosclerosis may also be caused/aggravated by activated macrophages, it is possible that the diagnosis/evaluation of these diseases could be aided by a folate-linked imaging/contrast agent. The avid folate conjugate uptake by activated macrophages in both arthritic joints and liver indicates that macrophages can be effectively targeted regardless of their anatomical location.

EXAMPLE 14

Immunotherapy Mediated Protection Against Adjuvant-Induced Arthritis

Figure 10:
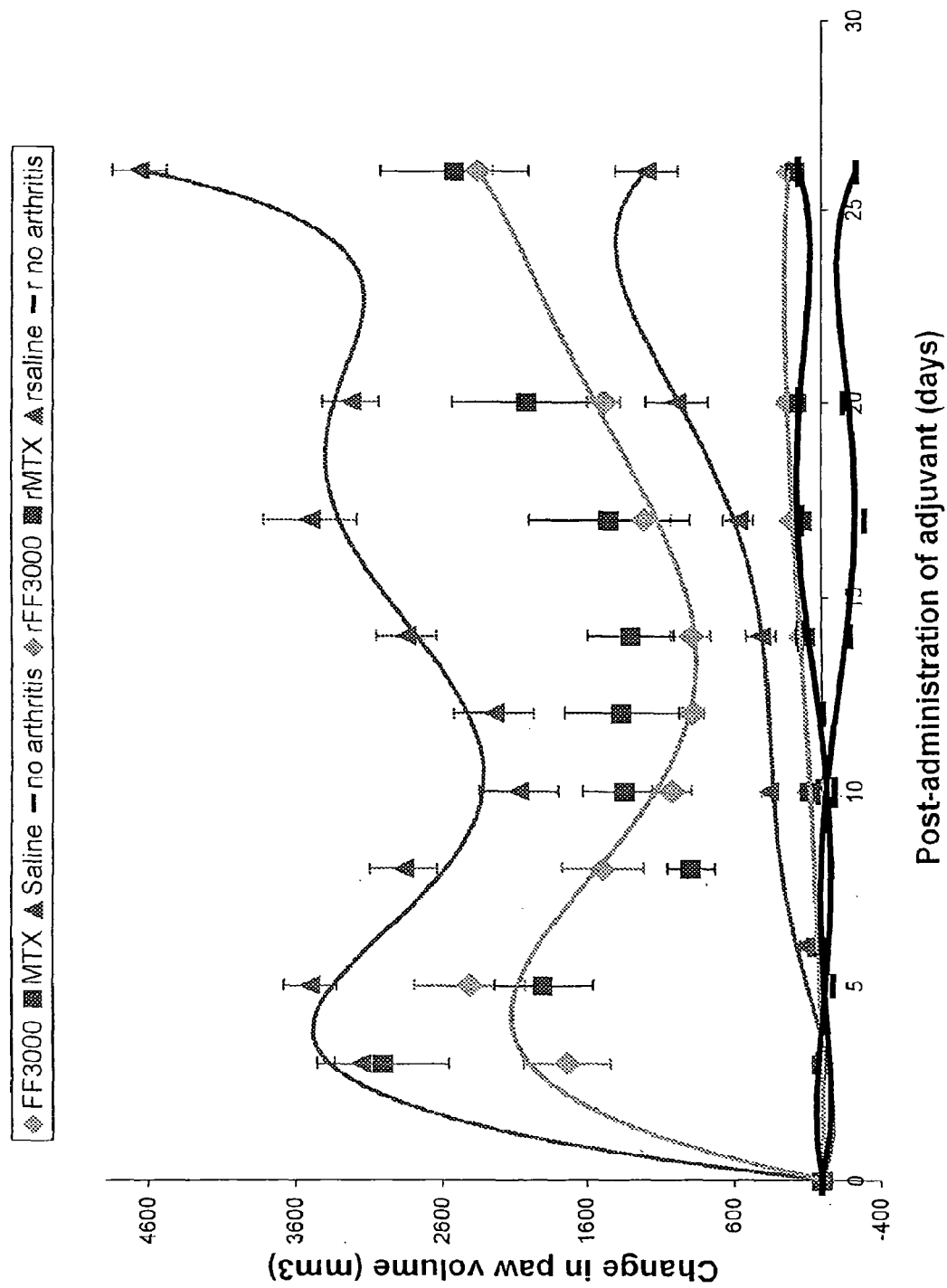
FIG. 10 demonstrates immunotherapy mediated protection against adjuvant-induced arthritis (light gray diamonds represent administration of folate-FITC, dark gray squares represent administration of methotrexate, dark gray triangles represent administration of saline, and black lines represent animals without arthritis). The bottom four lines represent the uninjected paw.

For the assay shown in FIG. 10, the protocol described in Example 8 was followed except that 3000 nmoles/kg of folate-FITC was administered per day (3 doses on days 1, 2, and 3) and folate-FITC was delivered using an osmotic pump implanted into the peritoneal cavity of the rat. Methotrexate (MTX) was administered at a dose of 0.15 mg by intraperitoneal injection one time per day on days 1, 8, and 15 after adjuvant administration. MTX was used in place of folate-FITC for animals treated with MTX. The results for both the left (injected) and right (uninjected) paw are shown. The results show that folate-FITC (FF) inhibits adjuvant-induced arthritis as well as MTX.

EXAMPLE 15

Immunotherapy Mediated Protection Against Adjuvant-Induced Arthritis

Figure 11:
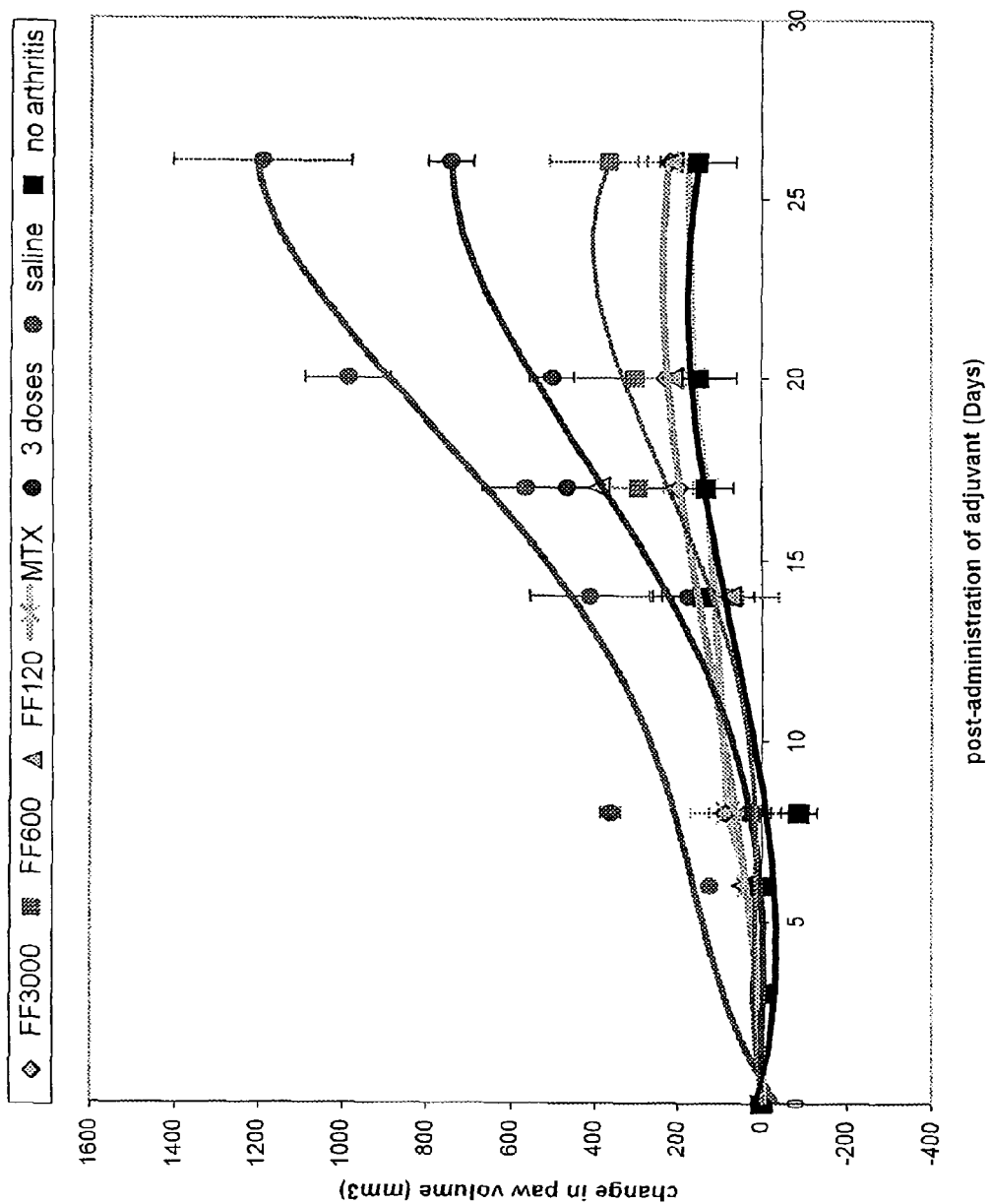
FIG. 11 demonstrates immunotherapy mediated protection against adjuvant-induced arthritis in the right (uninjected) paw (light gray diamonds represent administration of folate-FITC at 3000 nmoles/kg, light gray squares represent administration of folate-FITC at 600 nmoles/kg, light gray triangles represent administration of folate-FITC at 120 nmoles/kg, light gray x's represent administration of methotrexate, dark gray circles represent administration in 3 doses (as in Example 14), light gray circles represent administration of saline, and black squares represent animals without arthritis).

The protocol described in Example 14 was followed except that only the right paw volume was measured and folate-FITC (FF) was administered at doses of 3000, 600, and 120 nmoles/kg (FIG. 11). Also, FF was administered at 3000 nmoles/kg in either three doses as in Example 14 (indicated as "3 doses" in FIG. 11) or on days 1, 2, 3, 9, 11, and 14 as described in Example 8 (indicated as "FF3000" in FIG. 11). The results show that FF inhibits adjuvant-induced arthritis in the right paw of the arthritic rats (inflammation presumably appears in the uninjected right paw due to the systemic progression of arthritis), and that prolonged treatment with FF is more effective than 3 initial doses for treatment of adjuvant-induced arthritis.

EXAMPLE 16

Immunotherapy Mediated Protection Against Adjuvant-Induced Arthritis

Figure 12:
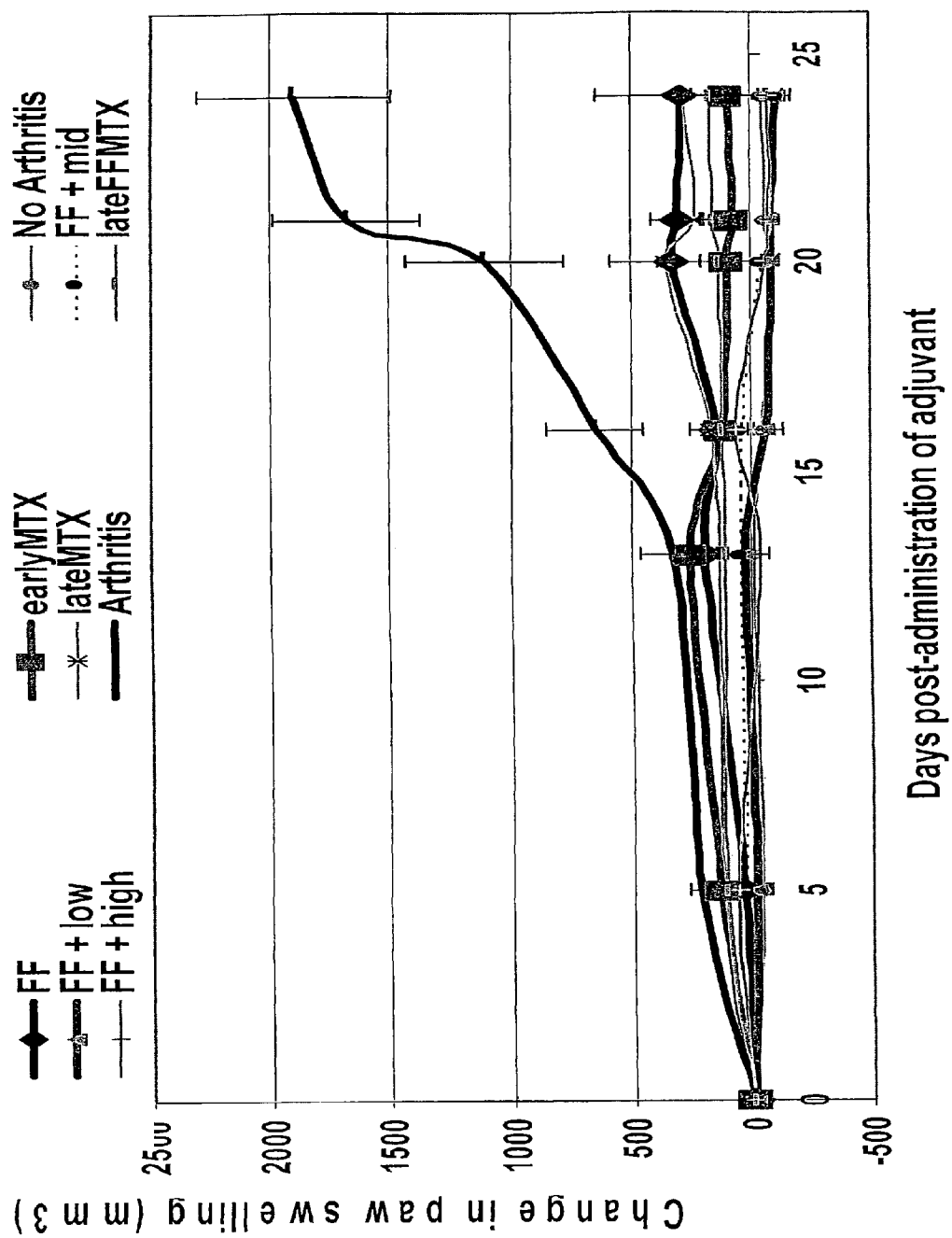
FIG. 12 demonstrates immunotherapy mediated protection against adjuvant-induced arthritis (black diamonds=FF, gray triangles=FF+low, vertical hash marks=FF+high, gray squares=early MTX, gray X's=late MTX, thick black lines=arthritis, gray circles=no arthritis, black circles=FF+mid, horizontal hash marks=late FFMTX).

The protocol described in Example 8 was followed except MTX was used at a dose of 0.15 mg (FF+low, early MTX, late MTX and lateFFMTX) to treat some animals in place of FF (see FIG. 12). Other animals were treated with 0.75 mg of MTX (FF+mid) or 1.5 mg of MTX (FF+high). For "early MTX" treatments, the rats were injected with MTX on days 1, 8, and 15 after arthritis induction. For "late MTX" treatments, the rats were injected with MTX on days 8 and 15 after adjuvant administration. All measurements were of the uninjected right paw. The results show that folate-FITC (FF) in combination with MTX (early or late treatments and a low, high, or middle dose of MTX) inhibits adjuvant-induced arthritis better than FF alone.

EXAMPLE 17

Immunotherapy Mediated Protection Against Adjuvant-Induced Arthritis

Figure 13:
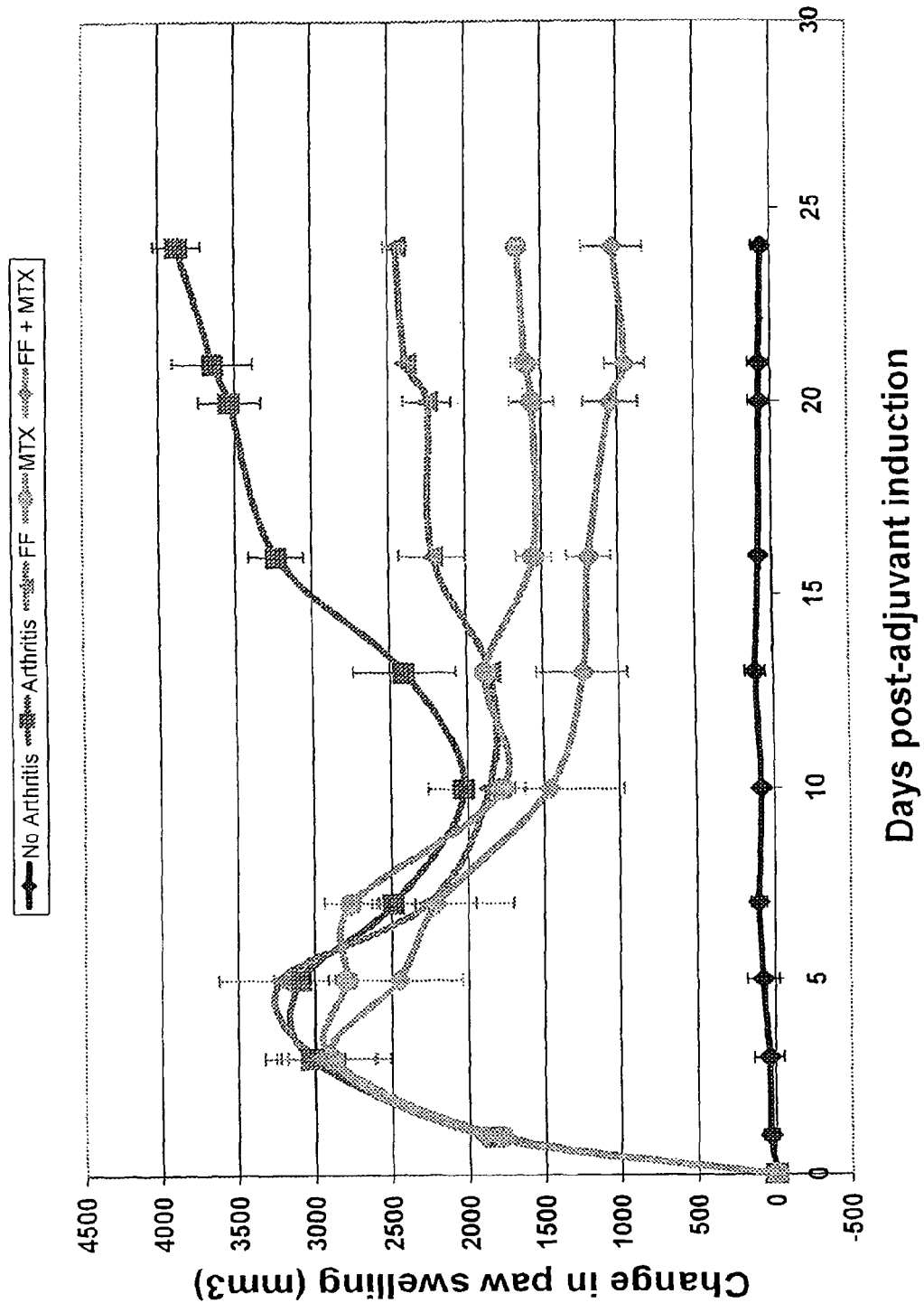
FIG. 13 demonstrates immunotherapy mediated protection against adjuvant-induced arthritis (black diamonds represent animals with no arthritis, dark gray squares represent animals with arthritis, light gray triangles represent administration of folate-FITC, light gray circles represent administration of methotrexate, and light gray diamonds represent administration of the combination of folate-FITC and methotrexate).

For the results shown in FIG. 13, the protocol described in Example 8 was followed except that some animals were treated with MTX alone (0.15 mg) on days 1, 8, and 15 after arthritis induction or were treated with MTX (0.15 mg; days 1, 8, and 15) in combination with FF as described in Example 14. The results show that the combination of FF and MTX inhibits adjuvant-induced arthritis to a greater extent than MTX or FF alone.

EXAMPLE 18

Immunotherapy Mediated Protection Against Adjuvant-Induced Arthritis

Figure 14:
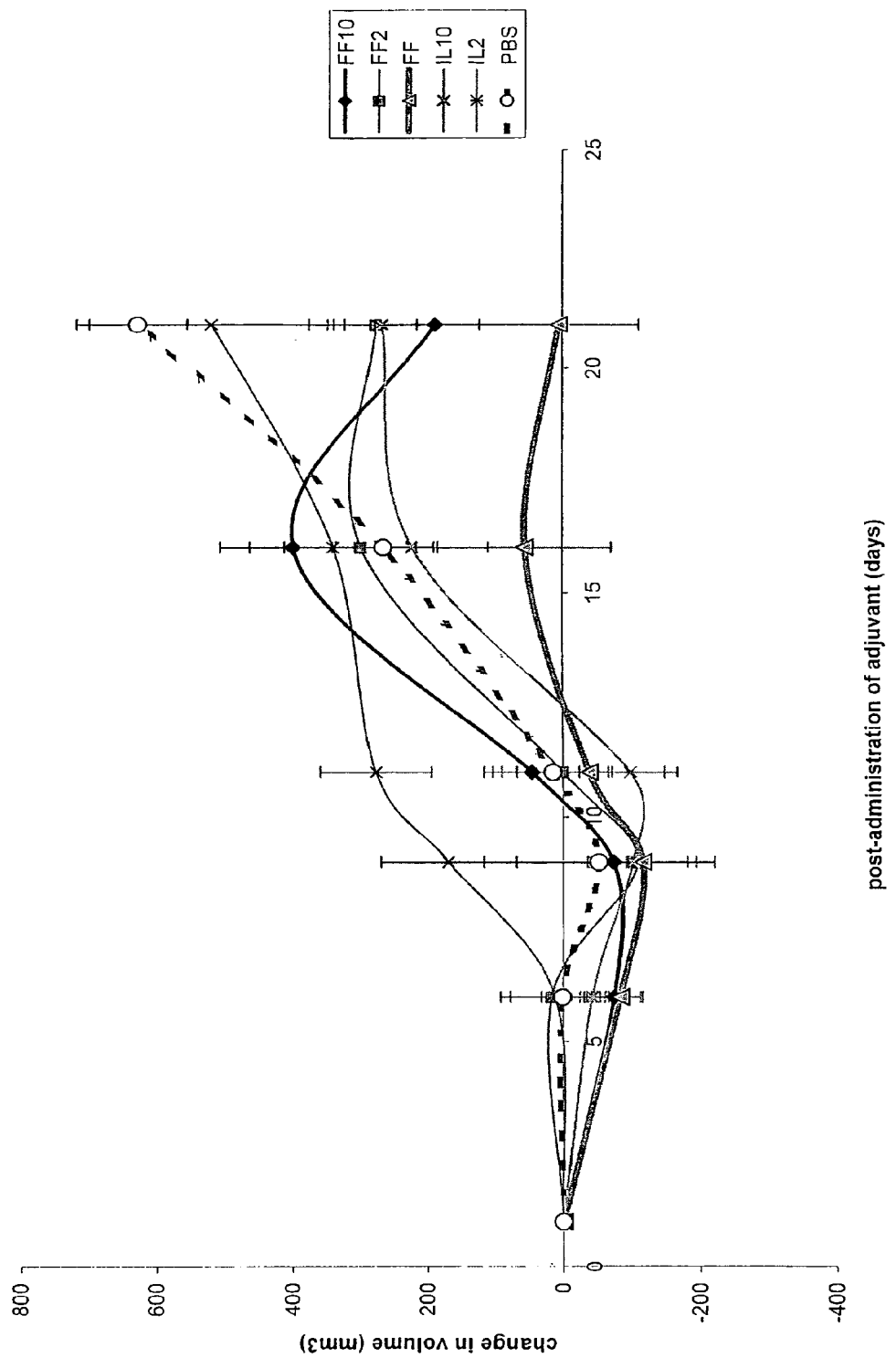
FIG. 14 demonstrates immunotherapy mediated protection against adjuvant-induced arthritis (black diamonds=FF10, gray squares=FF2, gray triangles=FF, gray X's=IL10, black X's=IL2, open circles=PBS).

The protocol described in Example 8 was followed except that IL-10 (10,000 U; FF10) or IL-2 (3 μg/kg; FF2) was administered along with the treatments with FF (i.e., the cytokines were administered by intraperitoneal injections on days 1, 2, 3, 9, 11, and 14 after adjuvant administration; see FIG. 14). The measurements made were measurements of the right, noninjected paw. The results show that either IL-10 or IL-2 prevent the inhibition of adjuvant-induced arthritis resulting from treatment with FF. All of the above immunotherapy results taken together indicate that folate-linked agents which are cytotoxic for macrophages can be used to treat macrophage-mediated disease states.

EXAMPLE 19

Folate-Targeted Imaging of Arthritic Rats

Figure 15:
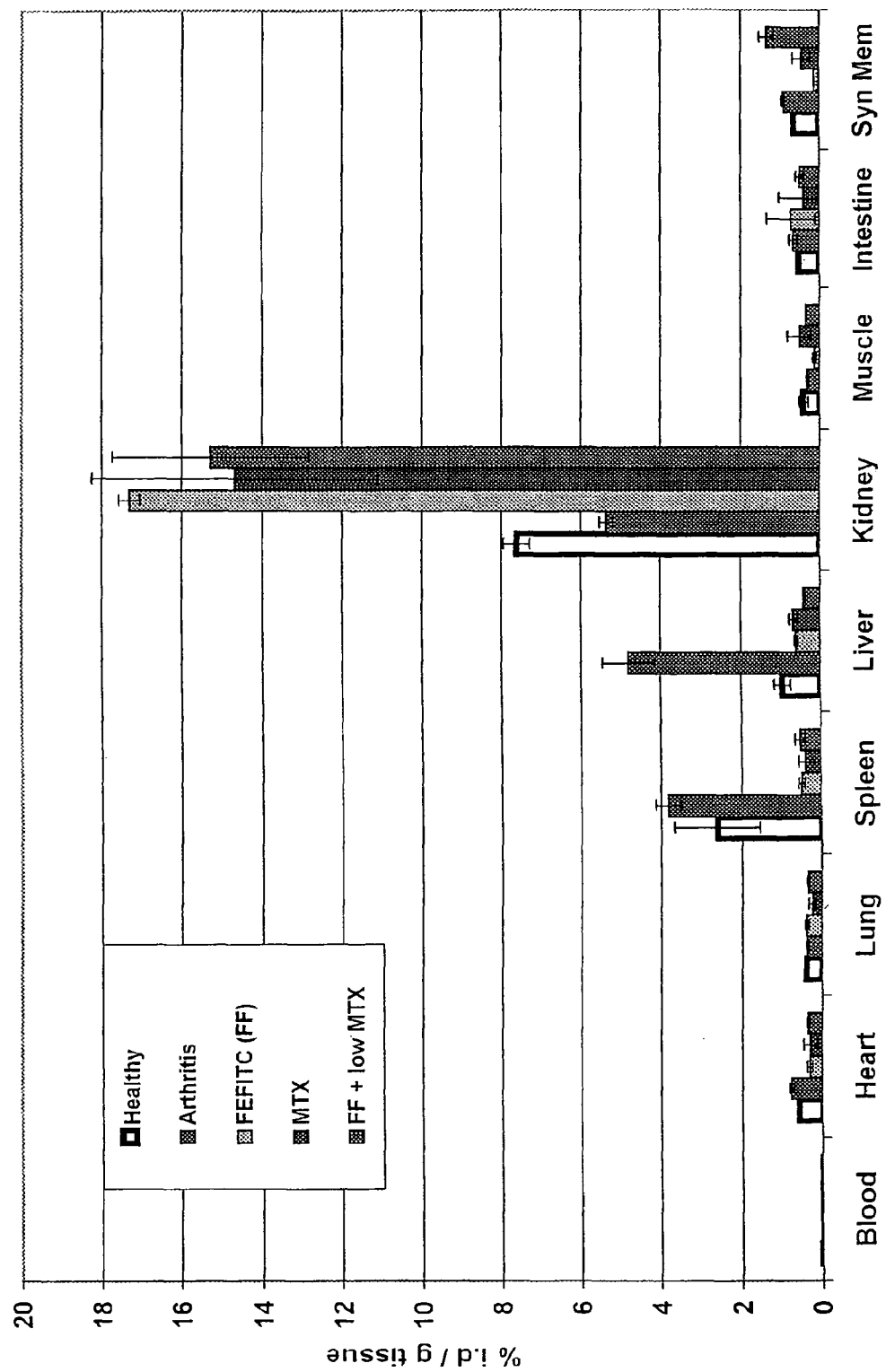
FIG. 15 shows folate-targeted imaging of arthritic rats ($1^{st}$ column=Healthy, $2^{nd}$ column=Arthritis, $3^{rd}$ column=FEFITC (FF), $4^{th}$ column=MTX, $5^{th}$ column=FF+low MTX).

For the assay shown in FIG. 15, the protocols were as described in Examples 2 and 4 except that some animals were treated with FF (2000 nmoles/kg; days 1, 2, 3, 9, 11, and 14) or MTX (0.15 mg; days 1, 8, and 15) as described in Examples 8 and 14, respectively. The results show that FF or MTX prevent EC20 uptake in all organs examined except the kidney. It is likely that EC20 uptake is reduced in most organs making more EC20 available for excretion through the kidney accounting for the increase in EC20 detected in kidney tissues.

The invention claimed is:

1. A method of monitoring/diagnosing a macrophage mediated disease state in vivo selected from the group consisting of arthritis, ulcerative colitis, Crohn's disease, inflammatory lesions, infections of the skin, osteomyelitis, organ transplant rejection, pulmonary fibrosis, sarcoidosis, psoriasis, systemic sclerosis, and any chronic inflammation, said method comprising the steps of, administering to a patient suffering from the macrophage mediated disease state an effective amount of a composition comprising a compound of the formula

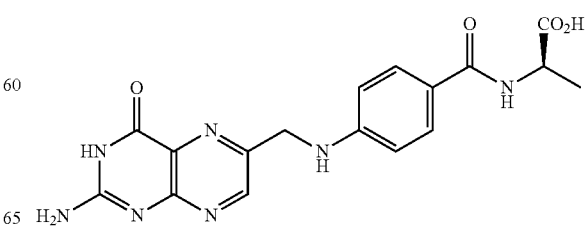

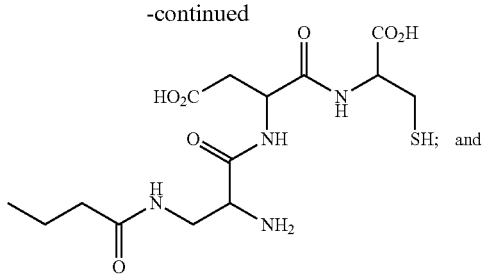
subjecting the patient to an imaging procedure to detect the compound localized at a site of the disease.
2. The method of claim 1 wherein the compound further comprises a metal cation.
3. The method of claim 2 wherein the metal cation is a radionuclide.
4. The method of claim 3 wherein the radionuclide is $^{99m}$Tc.
* * * * *